(12) United States Patent
Cvetovich et al.

(10) Patent No.: US 9,227,921 B2
(45) Date of Patent: Jan. 5, 2016

(54) SALTS AND POLYMORPHS OF A TETRACYCLINE COMPOUND

(71) Applicant: Paratek Pharmaceuticals, Inc., Boston, MA (US)

(72) Inventors: Raymond Cvetovich, Scotch Plains, NJ (US); Tadeusz Warchol, Northborough, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 245 days.

(21) Appl. No.: 13/749,101

(22) Filed: Jan. 24, 2013

(65) Prior Publication Data

US 2014/0005420 A1 Jan. 2, 2014

Related U.S. Application Data

(62) Division of application No. 12/471,758, filed on May 26, 2009, now Pat. No. 8,383,610.

(60) Provisional application No. 61/128,712, filed on May 23, 2008.

(51) Int. Cl.
  *C07C 237/26* (2006.01)
  *C07C 231/12* (2006.01)
  *C07C 309/30* (2006.01)
  *C07C 303/32* (2006.01)

(52) U.S. Cl.
  CPC ............. *C07C 231/12* (2013.01); *C07C 237/26* (2013.01); *C07C 303/32* (2013.01); *C07C 309/30* (2013.01); *C07B 2200/13* (2013.01); *C07C 2103/46* (2013.01)

(58) Field of Classification Search
  CPC .......................... C07C 237/26; C07B 2200/13
  USPC ........................................... 552/205
  See application file for complete search history.

*Primary Examiner* — Barbara P Badio
(74) *Attorney, Agent, or Firm* — McCarter & English, LLP; Elizabeth A. Hanley

(57) ABSTRACT

Crystalline forms, including salts and polymorphs, of a compound useful in the treatment of tetracycline compound-responsive states are provided herein. The crystalline compounds are useful for the treatment or prevention of conditions and disorders such as bacterial infections and neoplasms, as well as other known applications for tetracycline compounds in general.

20 Claims, 11 Drawing Sheets

SALTS AND POLYMORPHS OF A TETRACYCLINE COMPOUND

RELATED APPLICATION

This application is a divisional application of U.S. Ser. No. 12/471,758, filed on May 26, 2009, allowed, which claims priority to U.S. Ser. No. 61/128,712, filed on May 23, 2008, the entire contents of each of which are incorporated herein by reference.

BACKGROUND OF THE INVENTION

The development of the tetracycline antibiotics was the direct result of a systematic screening of soil specimens collected from many parts of the world for evidence of microorganisms capable of producing bactericidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454, 697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and *Salmonella*). The rise of tetracycline-resistant organisms has resulted in a general decline in use of tetracyclines and tetracycline analogue compositions as the antibiotic of choice.

Each pharmaceutical compound has an optimal therapeutic blood concentration and a lethal concentration. The bioavailability of the compound determines the dosage strength in the drug formulation necessary to obtain the ideal blood level. If the drug can crystallize as two or more polymorphs differing in bioavailability, the optimal dose will depend on the polymorph present in the formulation. Some drugs show a narrow margin between therapeutic and lethal concentrations. Chloramphenicol-3-palmitate (CAPP), for example, is a broad-spectrum antibiotic known to crystallize in at least three polymorphic forms and one amorphous form. The most stable form, A, is marketed. The difference in bioactivity between this polymorph and another form, B, is a factor of eight, thus creating the possibility of fatal overdosages of the compound if unwittingly administered as form B due to alterations during processing and/or storage. Therefore, regulatory agencies, such as the United States Food and Drug Administration, have begun to place tight controls on the polymorphic content of the active component in solid dosage forms. In general, for drugs that exist in polymorphic forms, if anything other than the pure, thermodynamically preferred polymorph is to be marketed, the regulatory agency may require batch-by-batch monitoring. Thus, it becomes important for both medical and commercial reasons to produce and market the pure drug in its most thermodynamically stable polymorph, substantially free of other kinetically favored polymorphs.

For instance, salt forms of a compound, and polymorphic forms of the free compound or salt, are known in the pharmaceutical art to affect, for example, the solubility, dissolution rate, bioavailability, chemical and physical stability, flowability, fractability, and compressibility of the compound as well as the safety and efficacy of drug products based on the compound (see, e.g., Knapman, Modern Drug Discovery, 2000, 3(2): 53).

Accordingly, identification of a salt form or free base of a compound with optimal physical and chemical properties will advance the development of tetracycline compounds as pharmaceuticals. The most useful of such physical and chemical properties include: easy and reproducible preparation, crystallinity, non-hygroscopicity, aqueous solubility, stability to visible and ultraviolet light, low rate of degradation under accelerated stability conditions of temperature and humidity, low rate of isomerization between isomeric forms, and safety for long-term administration to humans.

SUMMARY OF THE INVENTION

In one embodiment, the invention pertains, at least in part, to a stable solid state form, such as a crystalline form, of the aminoalkyl tetracycline compound, Compound 1:

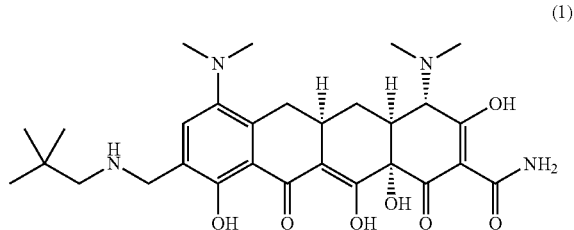 [SMILES: CN(C)c1cc(CNCC(C)(C)C)c(O)c2c1C[C@H]1C[C@H]3[C@H](N(C)C)C(O)=C(C(N)=O)C(=O)[C@@]3(O)C(O)=C1C2=O]

(1)

(4S,4AS,5AR,12AS)-4-7-Bis(dimethylamino)-9{[(2,2-dimethylpropyl)amino]methyl}-3,10,12,12A-tetrahydroxy-1, 1'-dioxo-1,4,4A,5,5A,6,11,12A-octahydrotetracene-2-carboxamide
(9-(2,2-dimethyl-propyl-aminomethyl)-minocycline).

In another embodiment, the invention pertains, at least in part, to an HCl salt of Compound 1. In another embodiment, the invention pertains, at least in part, to a tosylate (p-toluenesulfonate) salt of Compound 1. In another embodiment, the invention pertains, at least in part, to a mesylate salt of Compound 1

In another embodiment, the invention pertains, at least in part, to a stable crystalline form of Compound 1.

In another embodiment, the invention pertains, at least in part, to a stable crystalline form of a salt of Compound 1. For example, the stable crystalline form of a salt is a stable crystalline form of a tosylate, HCl or mesylate salt of Compound 1.

In another embodiment, the invention pertains, at least in part, to a polymorph of Compound 1.

In another embodiment, the invention pertains, at least in part, to a polymorph of a salt of Compound 1.

For example, the invention relates to a polymorph of a tosylate salt of Compound 1. The invention relates, in part to a form 1 polymorph of Compound 1. The invention relates, in part to a form 2 polymorph of Compound 1. The invention relates, in part to a form 3 polymorph of Compound 1.

For example, a form 1 polymorph of a tosylate salt of Compound 1 has X-ray powder diffraction peaks at approximately 8.06, 13.02, and 18.83 °2θ using Cu Kα radiation. In some embodiments, the form 1 polymorph of a tosylate salt of Compound 1 has X-ray powder diffraction peaks at approximately 8.06, 11.41, 13.02, 18.83, 20.54, and 24.53 °2θ using Cu Kα radiation. In some embodiments, the form 1 polymorph of a tosylate salt of Compound 1 has X-ray powder diffraction peaks at approximately 5.60, 8.06, 8.57, 11.41, 13.02, 15.58, 18.83, 20.54, and 24.53 °2θ using Cu Kα radiation.

For example, a form 1 polymorph of a tosylate salt of Compound 1 is stable at temperature in a range from about 0° C. to about 70° C. In some embodiments, the form 1 polymorph of a tosylate salt of Compound 1 is table at temperature in a range from about 5° C. to about 50° C. In some embodiments, the form 1 polymorph of a tosylate salt of Compound 1 is table at temperature in a range from about 20° C. to about 30° C.

The form 1 polymorph of a tosylate salt of Compound 1 can be obtained by crystallizing the tosylate salt of said Compound 1 from isopropanol.

For example, a form 2 polymorph of a tosylate salt of Compound 1 has X-ray powder diffraction pattern peaks at 7.82, 11.88, 16.12 and 21.46 °2θ using Cu Kα radiation.

For example, a form 3 polymorph of a tosylate salt of Compound 1 has X-ray powder diffraction pattern peaks at 5.11, 8.89, 10.34, 11.76 and 15.60 °2θ using Cu Kα radiation.

In yet another embodiment, the invention includes pharmaceutical compositions comprising a crystalline form of Compound 1 and a pharmaceutically acceptable diluent, excipient or carrier.

For example, the pharmaceutical composition of the invention includes a composition comprising a polymorph of Compound 1 and a pharmaceutically acceptable diluent, excipient or carrier.

In another embodiment, the pharmaceutical composition of the invention includes a salt of Compound 1 and a pharmaceutically acceptable diluent, excipient or carrier. For example, the salt can be an HCl salt, a tosylate salt, or a mesylate salt.

In one embodiment, the pharmaceutical composition of the invention includes a polymorph of a salt of Compound 1 and a pharmaceutically acceptable diluent, excipient or carrier. For example, the polymorph can be a polymorph of tosylate salt, HCl salt, or mesylate salt of Compound 1.

In some embodiments, the pharmaceutical composition comprises a polymorph of Compound 1, or salt thereof in a pure form.

In another embodiment, the pharmaceutical composition of the invention includes a polymorph of the tosylate salt of Compound 1 and a pharmaceutically acceptable diluent, excipient or carrier. For example, the polymorph can be a form 1, a form 2, or a form 3 polymorph of tosylate salt of Compound 1.

In some embodiments, the pharmaceutical composition comprises a polymorph of tosylate salt, HCl salt, or mesylate salt of Compound 1 in a pure form.

In another aspect of the invention, the salt of Compound 1 is more stable than the free base of Compound 1.

In another embodiment, the invention includes a method for preparing a stable crystalline form of Compound 1.

In another embodiment, the invention includes a method for preparing a stable crystalline form of a salt of Compound 1. For example, the stable crystalline can be a crystalline of a tosylate, HCl, or mesylate salt of Compound 1.

In another embodiment, the invention includes a method for preparing a polymorph of a salt of Compound 1. For example, the polymorph can be a polymorph of a tosylate, HCl, or mesylate salt of Compound 1.

In another embodiment, the invention includes a method for preparing a polymorph of a tosylate salt of Compound 1. For example, the polymorph can be a form 1, a form 2, or a form 3 polymorph of a tosylate salt of Compound 1.

In one embodiment, the invention includes a method for preparing a form 1 of polymorph of a tosylate salt of Compound 1, wherein the method comprises: combining Compound 1 with a solvent to produce a slurry; and adding p-toluenesulfonic acid. For example, the solvent can be an alcoholic solvent, such as isopropanol. The p-toluenesulfonic acid is provided in an amount of from 25 to 75 wt % relative to the amount of said Compound 1, for example, from 25 to 50 wt %, from 30 to 40 wt %, or 33 wt % relative to the amount of said Compound 1. For example, the p-toluenesulfonic acid is provided in a form of p-toluenesulfonic acid monohydrate For example, the slurry is warmed prior to the addition of p-toluenesulfonic acid.

For example, the slurry is stirred after the addition of p-toluenesulfonic acid. For example, the stirring is conducted at a temperature in a range from 20 to 25° C. For example, the stirring is conducted for 10 to 24 hours.

For example, the slurry is dried. For example, the water content of the supernatant of said slurry is in a range from 0.2 to 1.0 mg/mL, or in a range from 0.4 to 0.8 mg/mL.

In yet another embodiment, the invention includes a method for preparing a form 1 polymorph of a tosylate salt of Compound 1, wherein the method comprises: preparing a solution of Compound 1 in a solvent or a combination of solvents; and adding a solution of p-toluenesulfonic acid in a solvent or a combination of solvents.

For example, the solvent is an alcoholic solvent, such as methanol, ethanol, or isopropanol. For example, the combination of solvents includes an alcoholic solvent. For example, the combination of solvents further comprises a second alcoholic solvent. For example, the combination of solvents includes ethanol and isopropanol. For example, the combination of solvents further includes an anti-solvent, such as ketone, ether, and ester. For example, the ether includes, but is not limited to, methyl-t-butyl ether. For example, the combination of solvents includes an alcoholic solvent and an anti-solvent. For example, the combination of solvents includes methanol and methyl-t-butyl ether.

For example, p-toluenesulfonic acid is provided in an amount of from 25 to 75 wt %, from 30 to 50 wt %, from 35 to 45 wt %, or 40 wt % relative to the amount of said Compound 1. For example, p-toluenesulfonic acid is provided in a form of a p-toluenesulfonic acid monohydrate.

For example, the solution is prepared at a temperature in a range from 0 to 60° C., at a temperature in a range from 15 to 45° C., or at a temperature in a range from 20 to 25° C.

For example, the solution is warmed after it is prepared. For example, the solution is maintained at a temperature in a range from 20 to 50° C., or at about 45° C.

For example, the method further comprises adding a seed crystal of monotosylate salt of Compound 1 to produce a slurry. The slurry may be stirred for 10 to 24 hours or for about 22 hours. The slurry may be stirred at a temperature in a range from 15 to 45° C. or at about 20° C. The slurry may be dried. For example, the water content of the slurry is in a range of 1 to 10 wt %, or in a range of 2 to 6 wt %, or about 3 wt %.

In another embodiment, the invention includes a method for preparing a form 1 polymorph of a tosylate salt of Compound 1, wherein the method comprises: dissolving a freebase of Compound 1 in a first solvent or combination of solvents to form a first solution; dissolving p-toluenesulfonic acid in a second solvent or combination of solvents to form a second solution; and combining said first and second solution to form a third solution.

In one embodiment, the first and second solvent or combination of solvents can be the same or different. In another embodiment, the solvent can be an alcoholic solvent, such as methanol, ethanol, and isopropanol. In another embodiment, the combination of solvents is a combination of two alcoholic solvents, including, but not limited to ethanol and isopropanol. In a preferred example, the volume-to-volume ratio of ethanol and isopropanol is 2 to 1. In yet another embodiment, the combination of solvents is a combination includes, but is not limited to, an alcoholic solvent and an anti-solvent (e.g., a ketone, an ether, an ester, etc.). For example, the combination of solvents is a combination that includes, but is not limited to, methanol and methyl-t-butyl ether. In a preferred example, the volume-to-volume ratio of methanol and methyl-t-butyl ether is 1 to 1.2.

In another embodiment, the method further comprises adding a form 1 polymorph tosylate salt of Compound 1 to the third solution to form a fourth solution. For example, the form 1 polymorph tosylate salt is a seed crystal. In some embodiments, the fourth solution forms a slurry upon stirring. The slurry may be washed with a solvent or a combination of solvents, which may be the same or different from the first solvent or combination of solvent, or the second solvent or combination of solvents. The slurry may be dried.

In another embodiment, the invention relates to a pure composition comprising Compound 1, where in the composition is about 90-100%, preferably 95-100%, more preferably 98-100% (wt./wt.) or 99-100% (wt./wt.) pure; e.g. less than about 10%, less than about 5%, less than about 2% or less than about 1% impurity is present. Such impurities include, e.g., degradation products, oxidized products, epimers, solvents, and/or other undesirable impurities.

In yet another embodiment, the invention includes a method for treating a tetracycline responsive state in a subject, by administering to the subject an effective amount of a crystalline form of Compound 1. For example, the subject is a human subject.

In yet another embodiment, the invention includes a method for treating a tetracycline responsive state in a subject, by administering to the subject an effective amount of a stable salt of Compound 1. For example, the stable salt is a tosylate, an HCl, or a mesylate salt of Compound 1.

In yet another embodiment, the invention includes a method for treating a tetracycline responsive state in a subject, by administering to the subject an effective amount of a polymorph of Compound 1.

In yet another embodiment, the invention includes a method for treating a tetracycline responsive state in a subject, by administering to the subject an effective amount of a polymorph of salt of Compound 1. For example, the polymorph can be a polymorph of a tosylate, an HCl, or a mesylate salt of Compound 1.

In yet another embodiment, the invention includes a method for treating a tetracycline responsive state in a subject, by administering to the subject an effective amount of a polymorph of tosylate salt of Compound 1. For example, the polymorph of tosylate can be a form 1, a form 2, or a form 3 polymorph of tosylate salt of Compound 1.

For example, the tetracycline responsive state is a bacterial infection. The bacterial infection can be associated with gram positive bacteria, or gram negative bacteria. In some embodiments, the bacterial infection is associated with *E. coli, S. aureus,* or *E. faecalis*.

In some embodiments, the bacterial infection is resistant to other tetracycline antibiotics, which include, but are not limited to, tetracycline, minocycline, doxycycline, sancycline, chlortetracycline, demeclocycline, oxytetracycline, chelocardin, rolitetracycline, lymecycline, methacycline, apicycline, clomocycline, pipacycline, mepylcycline, meglucycline, guamecycline, penimocycline, and etamocycline.

DETAILED DESCRIPTION OF THE INVENTION

Figure 1:
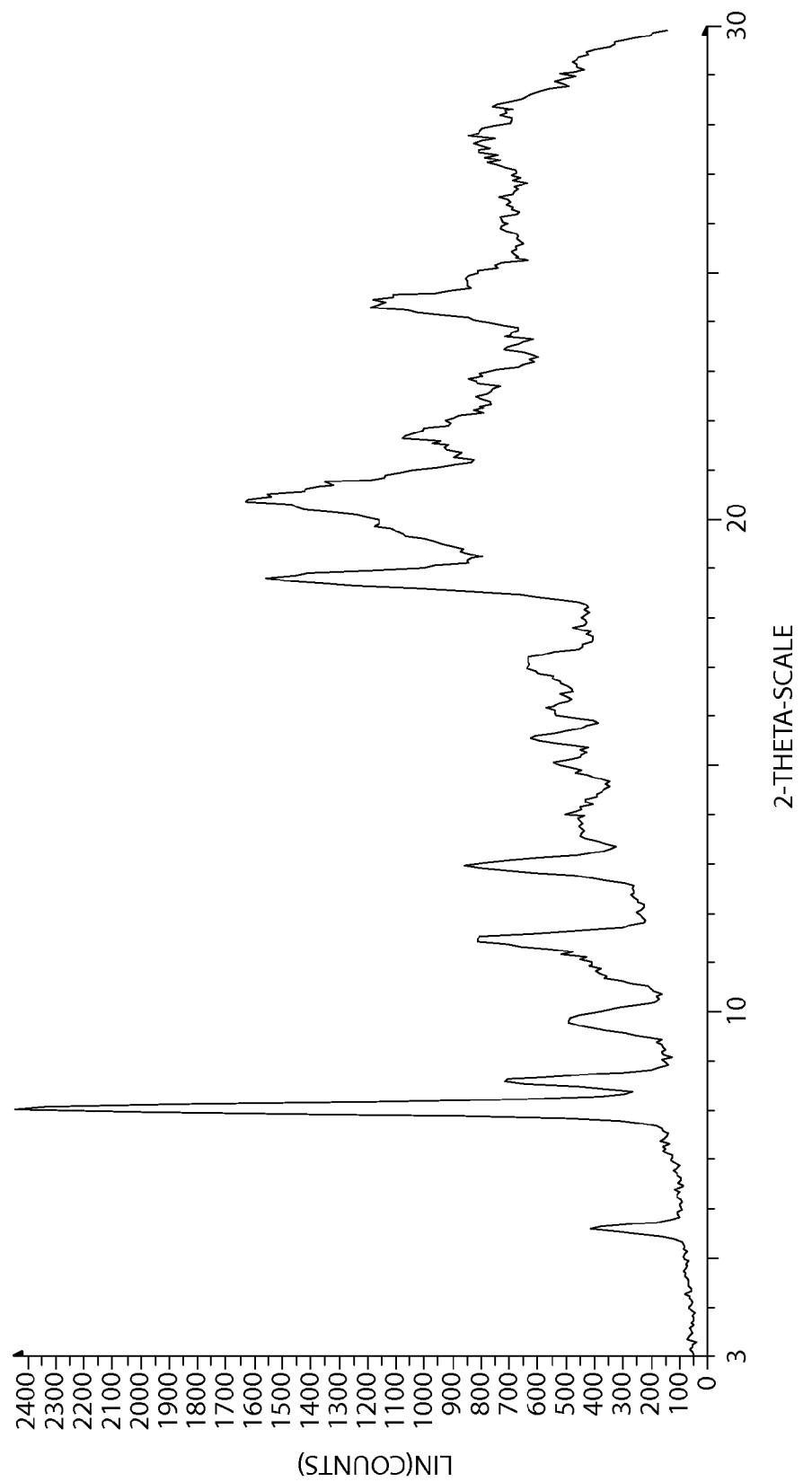
FIG. 1 provides an X-ray powder diffraction pattern of a sample comprising crystalline Compound 1 at 25° C.

Tetracycline-type antibiotic compounds have long been known to have limited stability in the solid phase freebase form. One such non-crystalline tetracycline analog compound, (4S,4AS,5AR,12AS)-4-7-Bis(dimethylamino)-9-{[(2,2-dimethylpropyl)amino]methyl}-3,10,12,12A-tetrahydroxy-1,1'-dioxo-1,4,4A,5,5A,6,11,12A-octahydrotetracene-2-carboxamide (Compound 1; MW=556.66, MF=C$_{29}$H$_{40}$N$_4$O$_7$), has limited stability in the solid phase upon exposure to air, light and/or moisture.

(1)

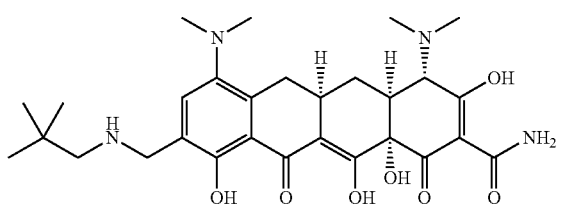

(4S,4AS,5AR,12AS)-4-7-Bis(dimethylamino)-9{[(2,2-dimethylpropyl)amino]methyl}-3,10,12,12A-tetrahydroxy-1,1'-dioxo-1,4,4A,5,5A,6,11,12A-octahydrotetracene-2-carboxamide.

Specifically, Compound 1 is a yellow amorphous solid that is unstable at temperatures higher than 0° C. and when exposed to air. Compound 1 must be stored at temperatures below 0° C. with limited exposure in the solid phase to air, light and moisture. Outside of these limited exposure conditions, Compound 1 degrades to produce degradation products including air degradation products 2, 3 and 4, as well as the 4-epi-isomer 5.

2

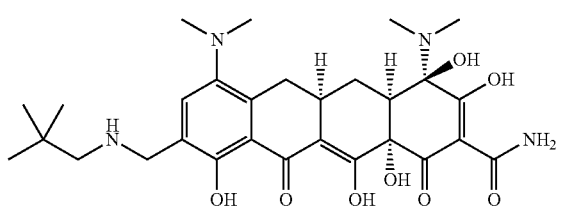

3

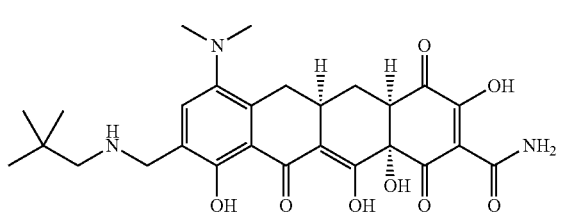

4

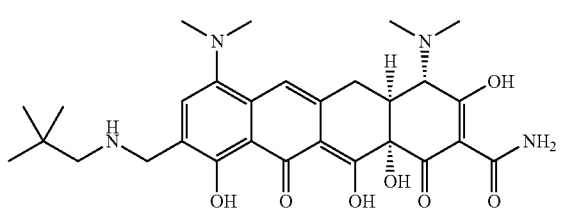

5

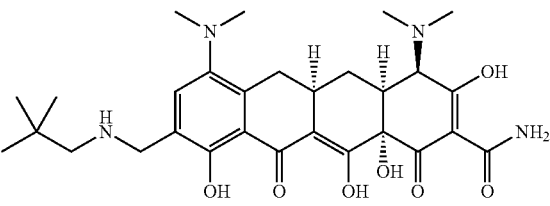

Prior to this disclosure, no stable crystalline forms or stable crystalline acid salts of Compound 1 were known.

The present invention relates to crystalline Compound 1, salt forms of Compound 1, polymorphic forms of Compound 1 or polymorphic forms of salts of Compound 1; pharmaceutical compositions comprising the crystalline forms, salt forms, polymorphic forms, or polymorphic forms of salts of Compound 1; methods of making the crystalline forms, salt forms, polymorphic forms, or polymorphic forms of salts of Compound 1; and methods of their use for the treatment of tetracycline-responsive states.

1. Solid Form Compounds

Compound 1 is a tetracycline compound. The term "tetracycline compound" includes many compounds with a similar ring structure to tetracycline. Examples of tetracycline compounds include: tetracycline, chlortetracycline, oxytetracycline, demeclocycline, methacycline, sancycline, doxycycline, and minocycline.

The free base and certain pharmaceutically acceptable salts of Compound 1 are described in U.S. application Ser. No. 10/786,881, corresponding to U.S. Publication. No. 2005/0026876 A1. There is no teaching or suggestion of crystalline forms of Compound 1, or that any of the described salt forms are superior to the others, as judged by the list of properties described above.

Thus, the present invention addresses the need for improved tetracycline compounds and the need for improved solid state forms of tetracycline compounds for manufacturing and bioavailability.

The solid state form of the tetracycline compound, Compound 1, can be a crystalline form. The crystalline form of the compound can be a free base. Crystalline forms of different salts of the free base compound can be formed. Examples of acids which can be used to convert the free base to a salt include, but are not limited to, HCl, p-toluenesulfonic acid, trifluoroacetic acid, methylsulfonic acid, benzenelsulfonic acid, and acetic acid.

The neutral forms of the compounds may be regenerated by contacting the salt with a base or acid and isolating the parent compound in the conventional manner. The parent form of the compound may differ from the various salt forms in certain physical properties, such as solubility in polar solvents.

As described herein, a process through which different crystalline forms of Compound 1 can be generated has been developed. More specifically, the inventors have shown that the crystalline form obtained mainly depends on the nature of the solvent used in the process. For the purposes of this description the term "crystalline form" refers to either a polymorphic form or a non-amorphous form, without distinction. "Polymorphic form" refers to an organized structure involving only molecules of the solute and having a characteristic crystalline signature.

The terms, "polymorphs" and "polymorphic forms" and related terms herein refer to crystalline forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Differences in stability can also result from changes in chemical reactivity (e.g., differential oxidation, such that a dosage form discolors more rapidly when comprised of one polymorph than when comprised of another polymorph) or mechanical property (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between polymorphs).

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

Techniques for characterizing polymorphs include, but are not limited to, differential scanning calorimetry (DSC), X-ray powder diffractometry (XRPD), single crystal X-ray diffractometry, vibrational spectroscopy, e.g., IR and Raman spectroscopy, solid state NMR, hot stage optical microscopy, scanning electron microscopy (SEM), electron crystallography and quantitative analysis, particle size analysis (PSA), surface area analysis, solubility studies and dissolution studies.

The term, "solvate", as used herein, refers to a crystal form of a substance which contains solvent. The term "hydrate" refers to a solvate wherein the solvent is water.

A desolvated solvate is a crystal form of a substance which can only be made by removing the solvent from a solvate.

The term, "amorphous form", as used herein, refers to a noncrystalline form of a substance.

As used herein, the term "pure" means about 90-100%, preferably 95-100%, more preferably 98-100% (wt./wt.) or 99-100% (wt./wt.) pure compound; e.g. less than about 10%, less than about 5%, less than about 2% or less than about 1% impurity is present. Such impurities include, e.g., degradation products, oxidized products, epimers, solvents, and/or other undesirable impurities.

As used herein, a compound is "stable" where significant amounts of degradation products are not observed under constant conditions of humidity, light exposure and at temperatures higher than 0° C. over a period of four weeks. A compound is not considered to be stable at a certain condition when degradation impurities appear or an area percentage of existing impurities begins to grow. The amount of degradation growth as a function of time is important in determining compound stability.

All ranges set forth herein are intended to encompass the indicated endpoints of the range as well as all included values and ranges, including those not specifically set forth.

The present invention is directed to crystalline forms, salt forms and polymorphs of Compound 1; compositions comprising the crystalline forms, salts and polymorphs alone or in combination with other active ingredients; methods of preparing the crystalline, salts and polymorphs; and methods of their use in the modulation of tetracycline compound receptive states. While not intending to be bound by any particular theory of operation, the storage stability, compressibility, density or dissolution properties of the crystalline forms, salts and polymorphs are beneficial for manufacturing, formulation and bio-availability of the tetracycline compound.

Preferred salts and polymorphs of the invention are those that are characterized by physical properties, e.g., stability, solubility, hygroscopicity and dissolution rate, appropriate for clinical and therapeutic dosage forms. Preferred polymorphs of the invention are those that are characterized by physical properties, e.g., crystal morphology, compressibility and hardness, suitable for manufacture of a solid dosage form. Such properties can be determined using techniques such as X-ray diffraction, microscopy, IR spectroscopy, thermal analysis and hygroscopicity analysis, as described herein and known in the art.

1.1 Salts of Compound 1

In one aspect, the present invention provides crystalline forms of particular pharmaceutically acceptable salts of Compound 1. This aspect of the invention provides crystalline forms of HCl, mesylate and tosylate salts of Compound 1:

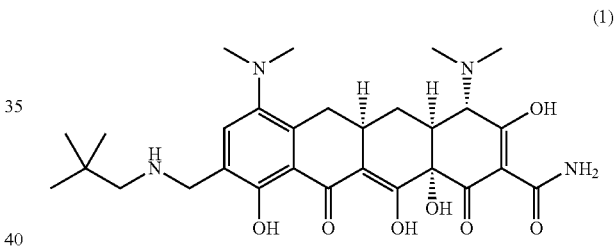

(1)

(4S,4AS,5AR,12AS)-4-7-Bis(dimethylamino)-9{[(2,2-dimethylpropyl)amino]methyl}-3,10,12,12A-tetrahydroxy-1, 1'-dioxo-1,4,4A,5,5A,6,11,12A-octahydrotetracene-2-carboxamide.

Each salt of the invention can be made from a preparation of Compound 1. Compound 1 can be synthesized or obtained according to any method apparent to those of skill in the art. In preferred embodiments, Compound 1 is prepared according to the methods described in detail in the examples below. See, e.g., U.S. Publication No. 2005/0026876 A1, the contents of which are hereby incorporated by reference in their entirety.

Alternatively, Compound 1 can be prepared by isolating a particular salt of Compound 1 and converting such a salt of Compound 1 to the neutral form by treatment with an appropriate base. For example, Compound 1 can be prepared by isolating the hydrochloride salt of Compound 1 by filtration, then converting it to the neutral form by treatment with monobasic sodium carbonate in ethyl acetate, or other suitable base.

Compound 1 prepared by any method can be contacted with an appropriate acid, either neat (i.e., free from admixture or dilution) or in a suitable inert solvent or solvents, to yield the salt forms of the invention. For example, Compound 1 can be contacted with a p-toluenesulfonic acid to yield the tosylate salt forms of the invention.

Stability studies were performed on the free base Compound 1 and an amorphous diHCl salt of Compound 1. This salt was formed by dissolving the compound in aqueous solution, adjusting the pH of the solution to approximately 4.2, followed by lyophilization. The free base degraded in less than one month at 40° C., and approximately three months at 4° C. In contrast, the diHCl salt of Compound 1 was stable for 6 months at 40° C., and for two years at room temperature (25° C.).

As shown in detail in the examples below, the tosylate salt of Compound 1, and polymorphs thereof, display desirable properties.

1.2 Polymorphs of Compound 1

The present invention also provides polymorphs of Compound 1. In certain embodiments, the polymorphs of the invention are polymorphs of the tosylate salt of Compound 1.

Each polymorph of the invention can be made from a preparation of Compound 1. Solid Compound 1 can be dissolved and then crystallized from the solvent mixtures described below to yield the polymorphic forms of the invention. In particular embodiments of the invention, a tosylate salt of Compound 1 can be dissolved and then crystallized from the solvent mixtures described below to yield certain polymorphic forms of the invention. In some embodiments of the invention, free base of Compound 1 can be dissolved and then acid is added to form a crystalline salt of Compound 1.

In one embodiment, the present invention provides a polymorph of a tosylate salt of Compound 1.

Figure 8:
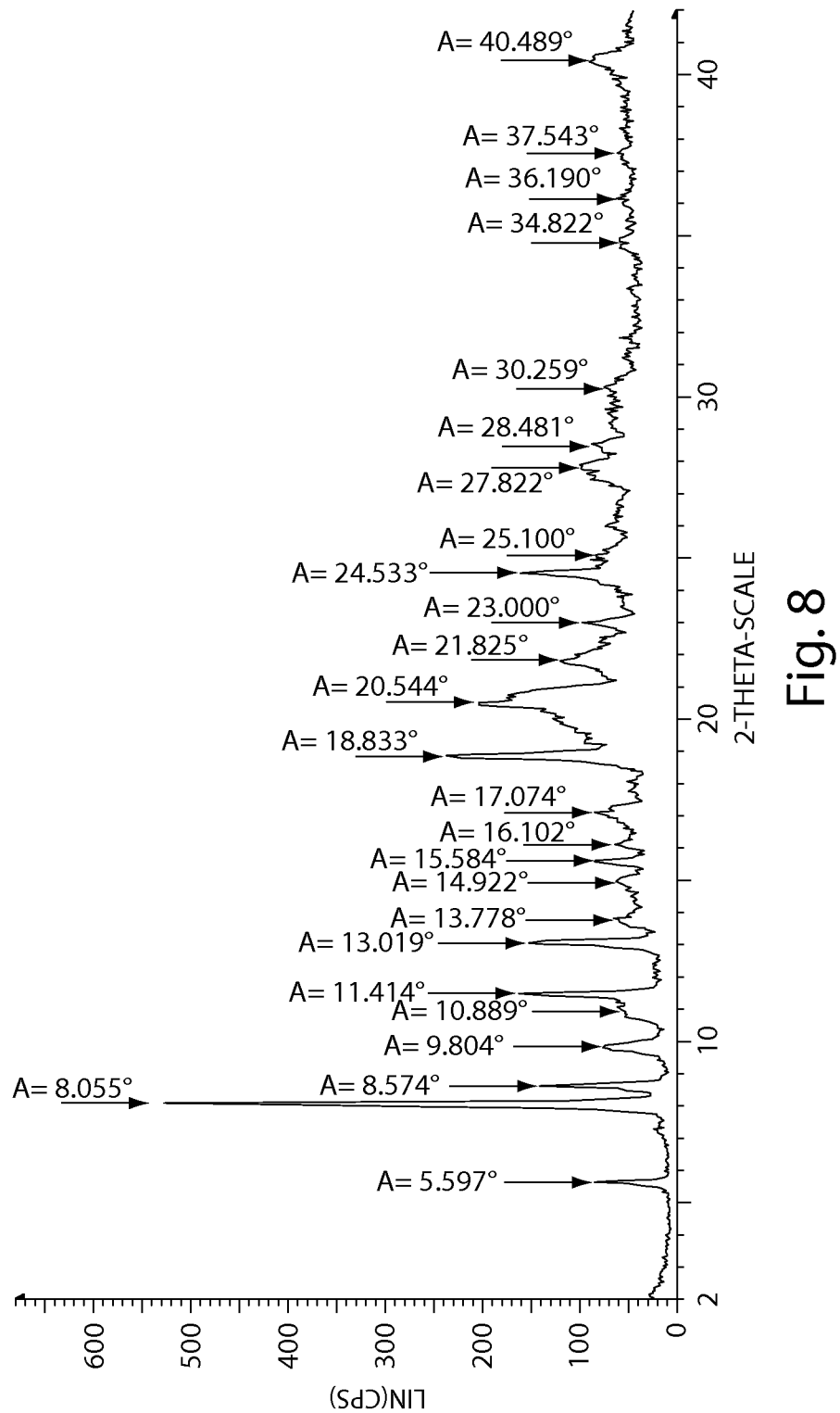
FIG. 8 provides a high resolution X-ray powder diffraction pattern of a sample comprising form 1 tosylate salt of Compound 1.

In a further embodiment, the invention provides a form 1 polymorph of the tosylate salt of Compound 1, having an X-ray powder diffraction pattern similar to that of FIG. 8, the characteristics of the diffraction pattern all shown in Table 1. For example, a particular form 1 polymorph of the invention has X-ray powder diffraction pattern peaks at 5.60, 8.06, 8.57, 11.41, 13.02, 15.58, 18.83, 20.54 and 24.53 °2θ using Cu Kα radiation. For example, a particular form 1 polymorph of the invention has X-ray powder diffraction pattern peaks at 8.06, 11.41, 13.02, 18.83, 20.54 and 24.53 °2θ using Cu Kα radiation. For example, a particular form 1 polymorph of the invention has X-ray powder diffraction pattern peaks at 8.06, 13.02, 18.83 and 24.53 °2θ. For example, a particular form 1 polymorph of the invention has major X-ray powder diffraction pattern peaks at 8.06 and 18.83 °2θ.

TABLE 1

| Angle (2-Theta °) | d value (Angstrom) | Intensity (Counts) | Intensity (%) |
|---|---|---|---|
| 5.60 | 15.78 | 347 | 15.9 |
| 8.06 | 10.97 | 2184 | 100.0 |
| 8.57 | 10.30 | 581 | 26.6 |
| 9.80 | 9.01 | 308 | 14.1 |
| 10.89 | 8.12 | 233 | 10.7 |
| 11.41 | 7.75 | 667 | 30.5 |
| 13.02 | 6.79 | 626 | 28.7 |
| 13.78 | 6.42 | 261 | 12.0 |
| 14.92 | 5.93 | 252 | 11.5 |
| 15.58 | 5.68 | 346 | 15.8 |
| 16.10 | 5.50 | 262 | 12.0 |
| 17.07 | 5.19 | 345 | 15.8 |
| 18.83 | 4.71 | 979 | 44.8 |
| 20.54 | 4.32 | 838 | 38.4 |
| 21.83 | 4.07 | 489 | 22.4 |
| 23.00 | 3.86 | 395 | 18.1 |
| 24.53 | 3.63 | 661 | 30.3 |
| 25.10 | 3.55 | 341 | 15.6 |
| 27.82 | 3.20 | 404 | 18.5 |
| 28.48 | 3.13 | 357 | 16.3 |

TABLE 1-continued

| Angle (2-Theta °) | d value (Angstrom) | Intensity (Counts) | Intensity (%) |
|---|---|---|---|
| 30.26 | 2.95 | 302 | 13.8 |
| 34.82 | 2.57 | 236 | 10.8 |
| 36.19 | 2.48 | 254 | 11.6 |
| 37.54 | 2.39 | 247 | 11.3 |
| 40.49 | 2.23 | 368 | 16.8 |

Figure 9:
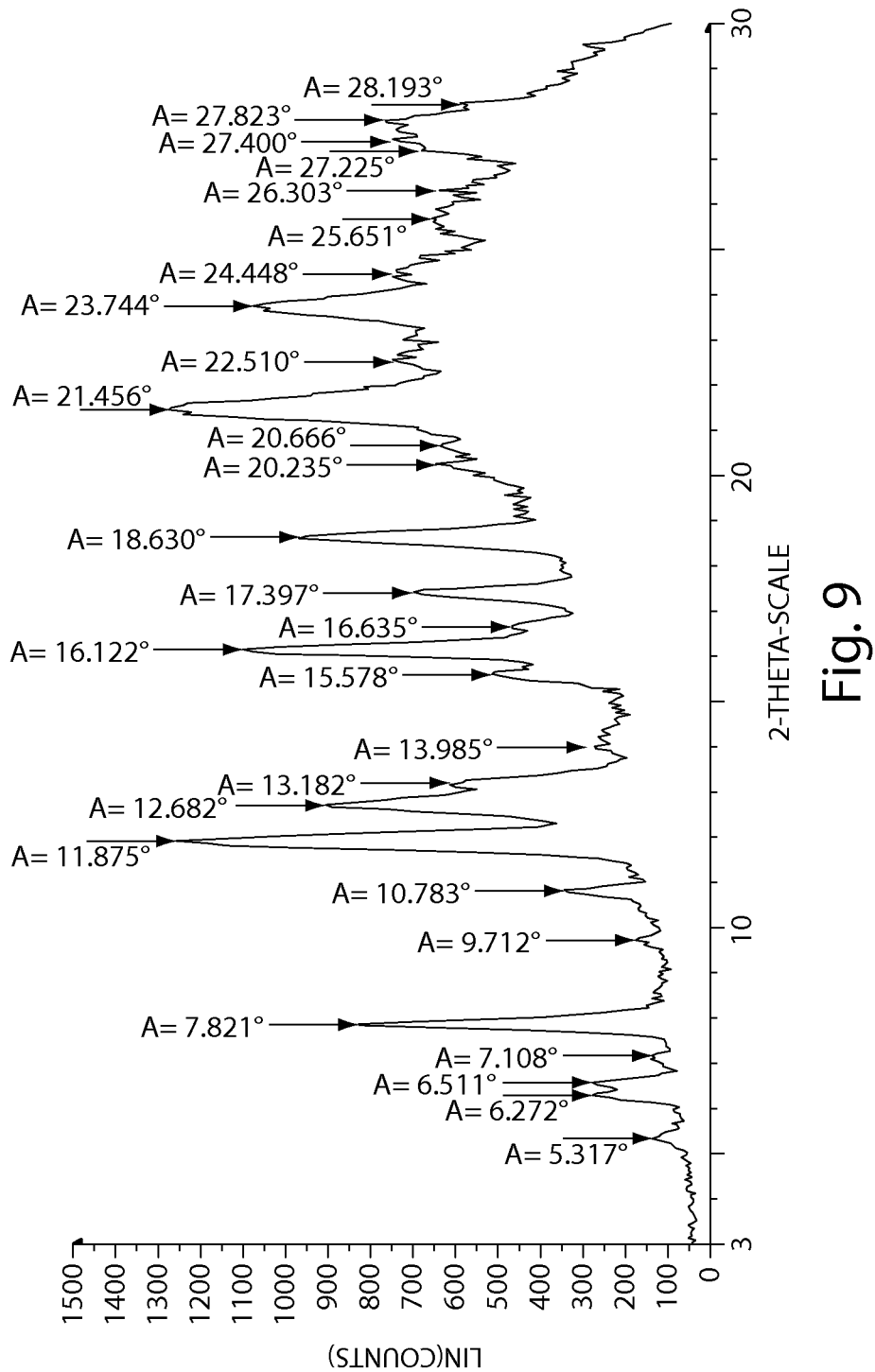
FIG. 9 provides a high resolution X-ray powder diffraction pattern of a sample comprising form 2 tosylate salt of Compound 1 (93.2% HPLC purity)

In another embodiment, the present invention provides form 2 of the tosylate salt of Compound 1. In one embodiment, the form 2 polymorph of the tosylate salt of Compound 1 has an X-ray powder diffraction pattern similar to that of FIG. 9, the characteristics of the diffraction pattern all shown in Table 2. For example, a particular form 2 polymorph of the invention has X-ray powder diffraction pattern peaks at 7.82, 11.88, 12.68, 16.12, 18.63, 21.46 and 23.74 °2θ using Cu Kα radiation. For example, a particular form 2 polymorph of the invention has major X-ray powder diffraction pattern peaks at 7.82, 11.88, 16.12 and 21.46 °2θ. For example, a particular form 2 polymorph of the invention has X-ray powder diffraction pattern peaks at 11.88 and 16.12 °2θ.

TABLE 2

| Angle (2-Theta °) | d value (Angstrom) | Intensity (Counts) | Intensity (%) |
|---|---|---|---|
| 5.317 | 16.62224 | 135 | 10.6 |
| 6.272 | 14.09246 | 275 | 21.5 |
| 6.511 | 13.57561 | 274 | 21.5 |
| 7.108 | 12.43554 | 137 | 10.8 |
| 7.821 | 11.30413 | 827 | 64.8 |
| 9.712 | 9.10741 | 173 | 13.5 |
| 10.783 | 8.20461 | 340 | 26.6 |
| 11.875 | 7.4528 | 1258 | 98.6 |
| 12.682 | 6.97995 | 904 | 70.8 |
| 13.182 | 6.7162 | 611 | 47.9 |
| 13.985 | 6.33261 | 299 | 23.4 |
| 15.578 | 5.68838 | 512 | 40.1 |
| 16.122 | 5.49766 | 1100 | 86.2 |
| 16.635 | 5.32915 | 467 | 36.6 |
| 17.397 | 5.09763 | 697 | 54.7 |
| 18.63 | 4.76275 | 967 | 75.8 |
| 20.235 | 4.38856 | 647 | 50.7 |
| 20.666 | 4.298 | 636 | 49.8 |
| 21.456 | 4.14147 | 1276 | 100 |
| 22.51 | 3.9499 | 747 | 58.6 |
| 23.744 | 3.7473 | 1076 | 84.3 |
| 24.448 | 3.64103 | 749 | 58.7 |
| 25.651 | 3.47293 | 652 | 51.1 |
| 26.303 | 3.38824 | 638 | 50 |
| 27.225 | 3.27554 | 678 | 53.2 |
| 27.4 | 3.25505 | 747 | 58.5 |
| 27.823 | 3.20648 | 763 | 59.8 |
| 28.193 | 3.16532 | 588 | 46.1 |

Figure 10:
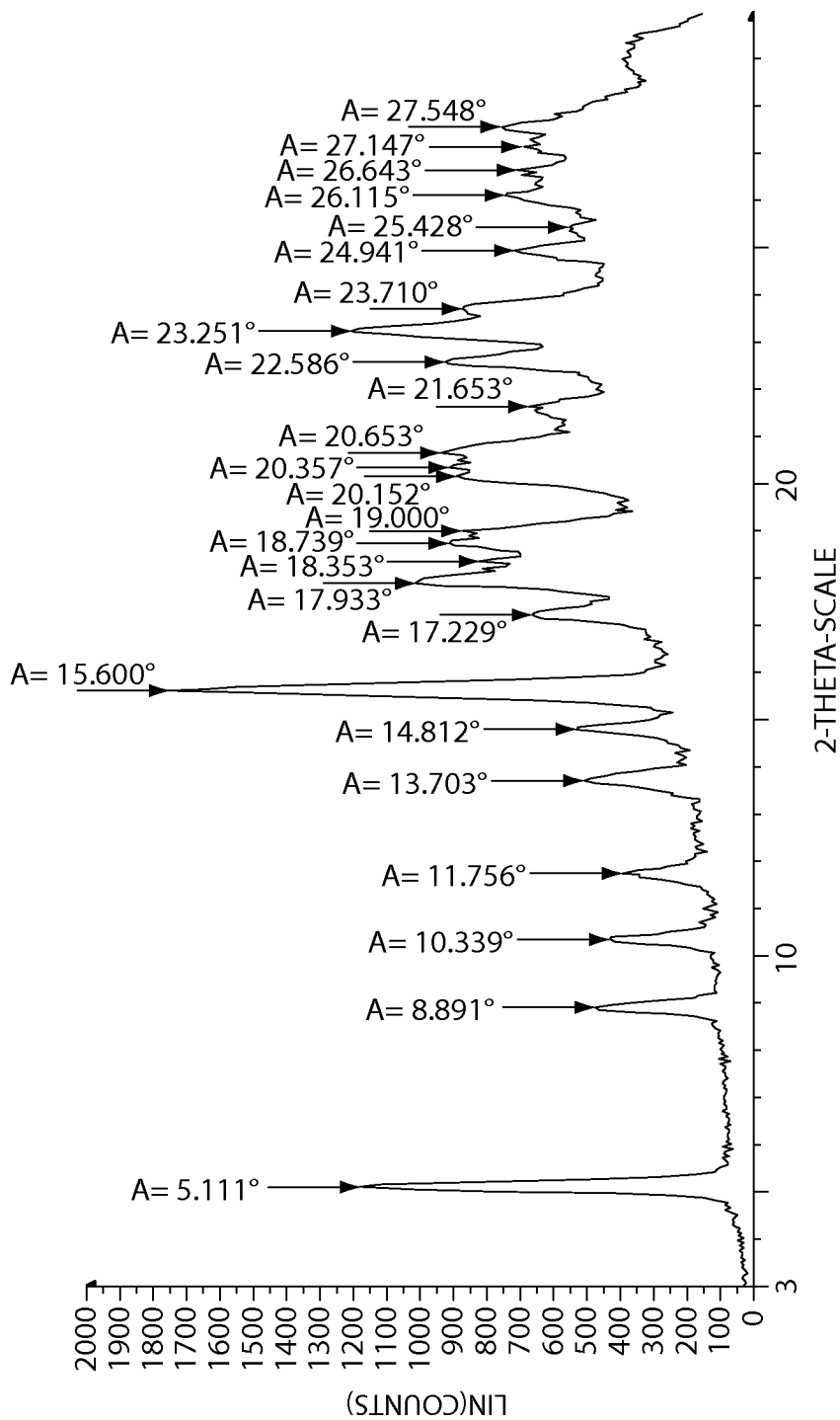
FIG. 10 provides a high resolution X-ray powder diffraction pattern of a sample comprising form 3 tosylate salt of Compound 1 (96.7% HPLC purity)

In yet another embodiment, the present invention provides form 3 of Compound 1. In further embodiments, the form 3 polymorph of the tosylate salt of Compound 1 has an X-ray powder diffraction pattern similar to that of FIG. 10, the characteristics of the diffraction pattern all shown in Table 3. For example, a particular form 3 polymorph of the invention has X-ray powder diffraction pattern peaks at 5.11, 8.89, 10.34, 11.76, 13.70, 14.81 and 15.60 °2θ using Cu Kα radiation. For example, a particular form 3 polymorph of the invention has major X-ray powder diffraction pattern peaks at 5.11, 8.89, 10.34, 11.76 and 15.60 °2θ. For example, a particular form 3 polymorph of the invention has major X-ray powder diffraction pattern peaks at 5.11 and 15.60 °2θ.

TABLE 3

| Angle (2-Theta °) | d value (Angstrom) | Intensity (Counts) | Intensity (%) |
|---|---|---|---|
| 5.11 | 17.29 | 1184 | 66.4 |
| 8.89 | 9.95 | 475 | 26.6 |
| 10.34 | 8.56 | 431 | 24.2 |
| 11.76 | 7.53 | 404 | 22.7 |
| 13.70 | 6.46 | 524 | 29.4 |
| 14.81 | 5.98 | 552 | 31 |
| 15.60 | 5.68 | 1783 | 100 |
| 17.23 | 5.15 | 661 | 37.1 |
| 17.93 | 4.95 | 1014 | 56.9 |
| 18.35 | 4.83 | 832 | 46.6 |
| 18.74 | 4.74 | 914 | 51.3 |
| 19.00 | 4.67 | 874 | 49 |
| 20.15 | 4.41 | 889 | 49.9 |
| 20.36 | 4.36 | 913 | 51.2 |
| 20.65 | 4.30 | 940 | 52.7 |
| 21.65 | 4.10 | 681 | 38.2 |
| 22.59 | 3.94 | 923 | 51.8 |
| 23.25 | 3.83 | 1206 | 67.7 |
| 23.71 | 3.75 | 872 | 48.9 |
| 24.94 | 3.57 | 718 | 40.3 |
| 25.43 | 3.50 | 551 | 30.9 |
| 26.12 | 3.41 | 745 | 41.8 |
| 26.64 | 3.35 | 709 | 39.8 |
| 27.15 | 3.28 | 689 | 38.7 |
| 27.55 | 3.24 | 754 | 42.3 |

The tosylate salt of Compound 1 crystallized as very small, irregular particles, typically 5-8 microns in size. FIG. 1 depicts X-ray powder diffraction (XRPD) of a crystalline solid of the tosylate salt of Compound 1. This compound was shown to melt at 190° C., followed by decomposition.

Gravimetric vapor sorption was performed on Compound 1 or its tosylate salt. It was determined that there were 2.5 molecules of water per molecule of Compound 1. XRPD was performed to compare the starting material (E00285) with the dehydrated material. The data indicated no change in form.

2. Synthesis of Compound 1

9-(aminomethyl)-minocycline dihydrochloride (200 mg, 1 eq.), DMF and trimethylacetaldehyde (45 µl eq.) were combined in 40 mL flasks and stirred. Triethylamine (150 µL, 3 eq.) was then added. After stirring at room temperature for several minutes, NaBH(OAc)$_3$ (175 mg, 2 eq.) and InCl$_3$ (9 mg, 0.1 eq.) was added. After one hour, the reaction was clear and red. Liquid chromatography showed a single product for the reaction. The reaction was quenched with methanol, the solvent was removed, and the product was purified using column chromatography.

Purification

Compound 1 was purified by chromatography by injecting an aqueous low pH solution of the compound into an HPLC in a polar organic solvent gradient, and combining the product fractions, such that the compound was purified. Selection of suitable acidic mobile phases enhanced process stability and selectivity. Organic and mineral acid mobile phases were effective at separating by-products including epimer impurities and closely-eluting by products through pH control or choice of acid. Acidic mobile phases also protected against oxidative degradation of the compound.

For example, the low pH solution had a pH of about 2-3. Examples of solutions that were used include 0.1% aqueous solutions of methane sulfonic acid and 0.1% aqueous solutions of trifluoroacetic acid. In certain embodiments, an isocratic gradient of 94% of the aqueous solution and 6% acetonitrile or another polar organic solvent were used to purify the compound from epimeric and closely eluting by-products.

The resulting aqueous product fractions may be combined and the pH may be adjusted to about 4.0-4.5 using a base (e.g., NaOH). Hydrophobic impurities and oxidative degradents of the compound may be removed by washing the aqueous solution with a non-polar organic solvent (e.g., $CH_2Cl_2$). The organic layers were discarded and the aqueous layers were combined and retained.

It should be noted that the organic solvents, such as methylene chloride, can be used to selectively remove late-eluting hydrophobic impurities such as 4-carbonyl by products and other oxidative degradents from the acidic aqueous solution of the compound.

The pH of the combined aqueous layers may then be adjusted to neutral pH, e.g., about 7.5 to about 8.5. The pH may be adjusted by the addition of a base, such as NaOH. The neutral solution was then washed with a non-polar organic solvent, such as methylene chloride. It should be noted that selective pH adjustment to neutral pH ranges also allowed the compound to be extracted into the organic solvent while retaining undesired β-epimer and by products in the aqueous phase.

In addition, antioxidants may also be added to the aqueous solutions of compounds described herein. The anti oxidants may be provided to prevent oxidative degradation of the compounds. Antioxidants such as ammonium sulfites or bisulfites can be used.

3. Methods of Preparing Polymorphic Forms of Compound 1

The invention also pertains to methods of preparing polymorphic forms of crystalline Compound 1.

In one embodiment, form 1 of the tosylate salt of Compound 1 can be made by any method of making form 1 apparent to those of skill in the art based upon the teachings herein. In certain embodiments, form 1 can be formed from maturation of the amorphous tosylate salt of Compound 1 in isopropanol, acetone, ethyl acetate, methyl pentanone, toluene or acetonitrile solution. Form 1 can also be obtained from recrystallization of the amorphous tosylate salt slurried in isopropanol. Form 1 can also be obtained by dissolving the freebase in an appropriate solvent or combination of solvents such as two alcohols or an alcohol and an anti-solvent such as a ketone, ether, ester, etc. After addition of the acid, the salt can be crystallized slowly in the correct form.

Solvent system in which impurities and free base of Compound 1 are soluble while the stable crystalline salt of Compound 1 is insoluble, e.g., crystalline slurry can be formed by precipitation, can be selected.

In another embodiment, form 2 of the tosylate salt of Compound 1 can be made by any method of making form 2 apparent to those of skill in the art based upon the teachings herein. In certain embodiments, form 2 can be formed from maturation of the amorphous tosylate salt of Compound 1 in dichloromethane.

In another embodiment, form 3 of the tosylate salt of Compound 1 can be made by any method of making form 3 apparent to those of skill in the art based upon the teachings herein. In certain embodiments, form 3 can be formed from maturation of the amorphous tosylate salt of Compound 1 in methyl ethyl ketone, ethyl acetate or methyl pentanone. Form 3 can also be obtained from maturation of form 1 in methyl pentanone.

In a further embodiment, the polymorphic forms of tosylate salt of Compound 1 described above may be produced by methods that include steps of combining Compound 1 with a solvent to produce a slurry, and adding p-toluenesulfonic acid.

Any suitable solvent may be used to create the slurry. Solvents that may be used in embodiments include alcoholic solvents, such as isopropanol. Any suitable combination of solvent may be used to create the solution from which the salt crystallizes. Solvent combinations that may be used in embodiments include, but are not limited to, methanol and methyl-t-butyl ether or ethanol and isopropanol.

For example, a slurry of Compound 1 in a solvent or a combination of solvents may be produced at a temperature from about 0° C. to about 60° C., such as from about 15° C. to about 45° C., or from about 20° C. to about 25° C. After it is produced, the slurry may optionally be warmed and/or maintained at a temperature from about 15° C. to about 60° C., such as from about 20° C. to about 50° C., or about 45° C.

Once the slurry is created, the p-toluenesulfonic acid may be added in an amount sufficient to produce a p-toluenesulfonic acid salt of Compound 1. In one embodiment, the p-toluenesulfonic acid is provided in an amount from about 25 to about 75 wt %, from about 25 to about 50 wt %, from about 30 to about 40 wt %, or about 33 wt % relative to the amount of Compound 1. The p-toluenesulfonic acid may be added in the form of a p-toluenesulfonic acid monohydrate.

Polymorphic forms of the tosylate salt of Compound 1 can be formed by a solution method. For example, a solution of Compound 1 may be produced at a temperature from about 0° C. to about 60° C., such as from about 15° C. to about 45° C., or from about 20° C. to about 25° C. After it is produced, the solution may optionally be warmed and/or maintained at a temperature from about 15° C. to about 60° C., such as from about 20° C. to about 50° C., or about 45° C.

Once the solution is created, the p-toluenesulfonic acid may be added in an amount sufficient to produce a p-toluenesulfonic acid salt of Compound 1. In one embodiment, the p-toluenesulfonic acid is provided in an amount from about 25 to about 75 wt %, from about 30 to about 50 wt %, from about 35 to about 45 wt %, or about 40 wt % relative to the amount of Compound 1. The p-toluenesulfonic acid may be added in the form of a p-toluenesulfonic acid monohydrate.

In one embodiment, form 1 polymorph used to seed the solution may be added. Any suitable solvent may be used to form the p-toluenesulfonic acid solution. Suitable solvents include alcoholic solvents, such as isopropanol or solvent combinations such as methanol and methyl-t-butyl ether. In a preferred embodiment, the vol./vol. ratio of methanol to methyl-t-butyl ether is 1:1.2. Suitable solvents include a combination of two or more alcoholic solvents, such as a combination of ethanol and isopropanol. In a preferred embodiment, the vol./vol. ratio of ethanol to isopropanol is 2:1. In particular embodiments, the p-toluenesulfonic acid solution includes the same solvent used to create the slurry or the solution of Compound 1.

After addition of p-toluenesulfonic acid in the appropriate solvent, a slurry of the form 1 polymorph of the tosylate salt of Compound is formed. The water content of the supernatant of the slurry may be adjusted to a suitable level following the addition of the p-toluenesulfonic acid. Typically, the water content of the slurry supernatant may be in a range from about 0.2 to about 1.0 mg/mL, such as from about 0.4 to about 0.8 mg/mL, e.g., about 0.6 mg/mL, about 0.54 mg/mL, etc.

Following the addition of the p-toluenesulfonic acid, the slurry or the solution may be stirred to produce a crystalline slurry. Stirring may be conducted for more than 48 hours. However, stirring is typically conducted for a period of from about 5 to about 36 hours, such as from about 10 to about 24 hours or about 18 hours.

Stirring may be conducted at any temperature suitable for producing the crystalline slurry. For example, the slurry may be stirred at a temperature from about 0° C. to about 60° C., such as from about 15° C. to about 45° C. or from about 20° C. to about 25° C.

After crystal formation, the crystalline slurry may be filtered to remove the supernatant, and the crystals may be washed with any suitable solvent. In embodiments, the crystals may be washed one to four times, and the solvent may be any solvent suitable for the preparation of the crystalline slurry. In particular, the solvent used to wash the crystals may be the same solvent or solvents used to form the original slurry or solution, or the p-toluenesulfonic acid solution.

The crystals produced may then be dried to remove excess solvent by any suitable method. For example, drying may be accomplished by one or more methods including but not limited to elevated temperatures in a range from about 0° C. to about 60° C., such as from about 15° C. to about 45° C.; blowing dry nitrogen over the crystals; and blowing humidified nitrogen over the crystals.

Figure 2:
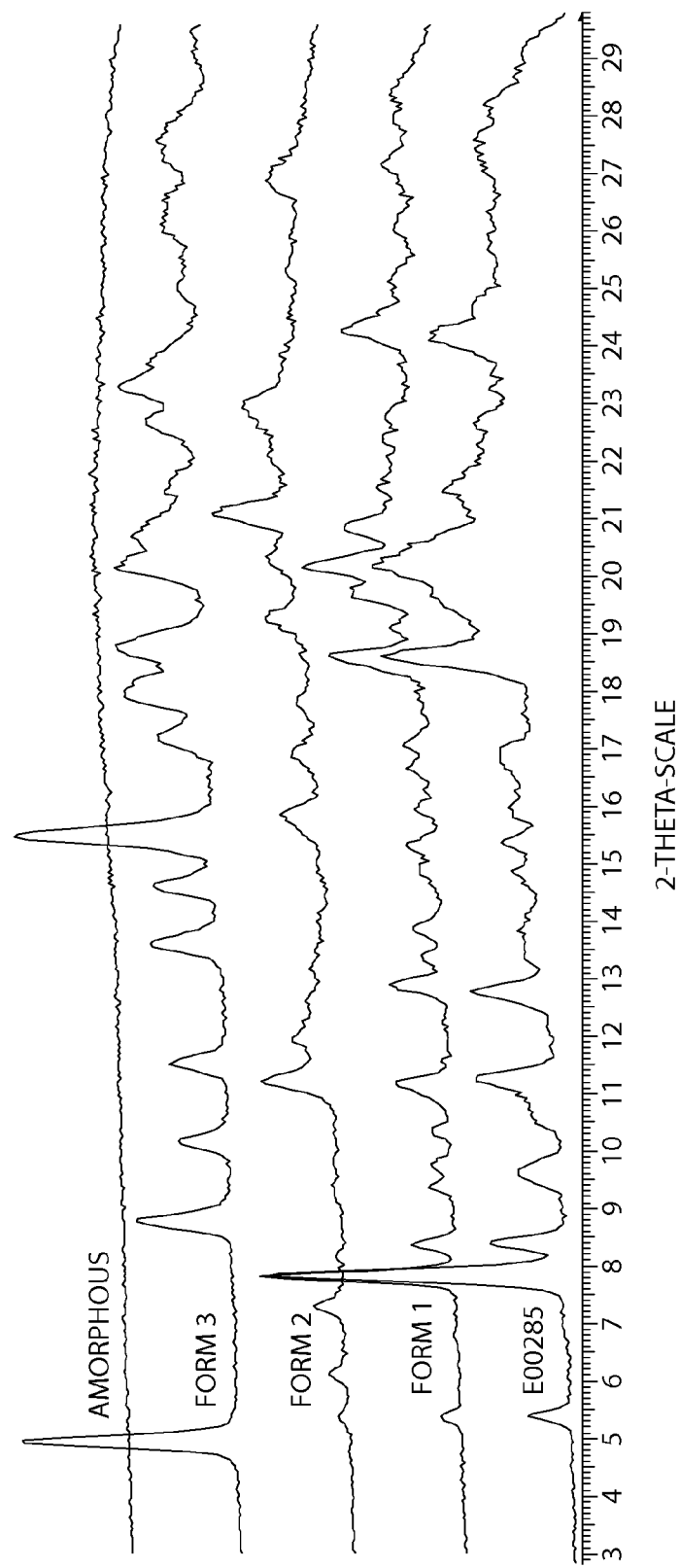
FIG. 2 provides an X-ray powder diffraction pattern at 25° C. of the starting material (E00285), form 1 tosylate salt, form 2 tosylate salt, form 3 tosylate salt, and the amorphous tosylate salt form of Compound 1.

Maturation studies were performed in which a sample of the tosylate salt of Compound 1 was slurried in different solvents, filtered, and the wet solid was analyzed by XRPD. Three polymorphic forms of the tosylate salt of Compound 1 were observed. FIG. 2 depicts the XRPD spectra of the starting material (E00285), form 1 tosylate salt, form 2 tosylate salt, form 3 tosylate salt, and the amorphous form of Compound 1.

Table 4 lists the solvents used for maturation experiments.

TABLE 4

| Example No. | Solvent | Form |
|---|---|---|
| 1 | water | Form 1 |
| 2 | nitromethane | Amorphous |
| 3 | anisole | Form 2 |
| 4 | 2-propanol | Form 1 |
| 5 | methylethyl ketone | Form 3 |
| 6 | acetone | Form 1 |
| 7 | ethyl acetate | Form 1 |
| 8 | dioxane | Amorphous |
| 9 | acetonitrile | Form 1 |
| 10 | toluene | Form 1 |
| 11 | dichloromethane | Form 2 |
| 12 | chloroform | Amorphous |
| 13 | TBME | Amorphous |
| 14 | isopropyl acetate | Form 2 |
| 15 | NMP | dissolved |
| 16 | 4-methyl-2-pentanone | Form 3 |
| 17 | THF | Gum |
| 18 | 10% EtOAc/cyclohexane | Amorphous |
| 19 | 10% water EtOH | Amorphous |
| 20 | 10% water/THF | Amorphous |
| 21 | 10% water/ACN | Amorphous |
| 22 | 10% water/2-propanol | Amorphous |
| 23 | 10% water/acetone | Amorphous |
| 24 | 10% water/dioxane | Amorphous |

Figure 3:
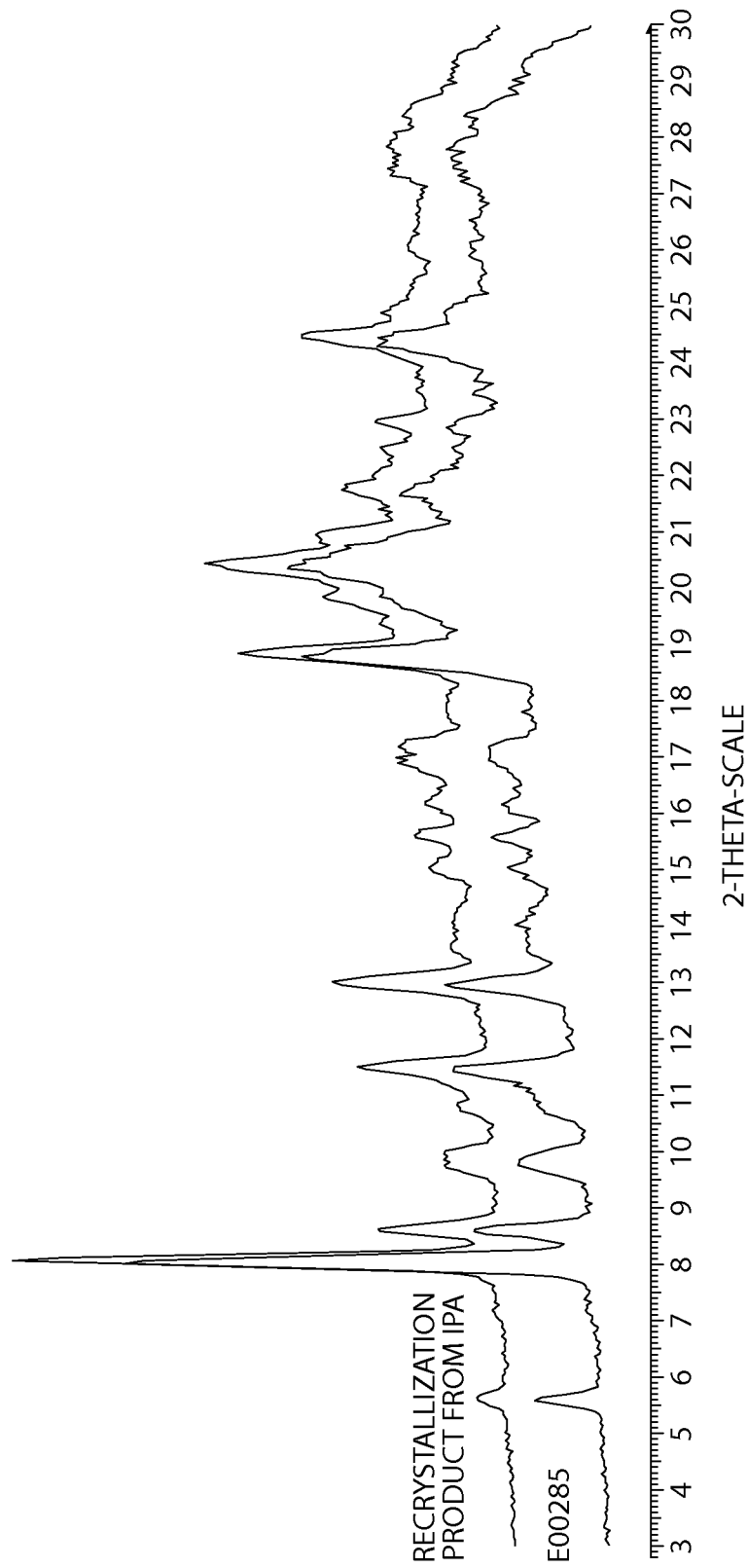
FIG. 3 provides a comparison of X-ray powder diffraction patterns at 25° C. for crystalline Compound 1 (E00285) and a sample comprising form 1 tosylate salt, obtained from recrystallization of amorphous tosylate salt of Compound 1 in IPA.

Recrystallization of the amorphous material of Compound 1 was performed in various solvents. Only recrystallization in 2-propanol (isopropyl alcohol, IPA) gave form 1 tosylate salt, as shown in Table 5. FIG. 3 compares XRPD spectra of reference Compound 1 (E00285) and the recrystallized form 1 tosylate salt from IPA.

TABLE 5

| Experiment No. | Solvent | Volume | At 50° C. | XRPD of precipitate of solid |
|---|---|---|---|---|
| 1 | nitromethane | 24 | Soluble | |
| 2 | anisole | 200 | Insoluble | Amorphous |
| 3 | 2-propanol | 60 | Soluble | Form 1 |
| 4 | methylethyl ketone | 100 | Soluble | Amorphous |
| 5 | acetone | 80 | Soluble | Amorphous |
| 6 | ethyl acetate | 200 | Insoluble | Amorphous |
| 7 | dioxane | 120 | Soluble | Amorphous |
| 8 | acetonitrile | 80 | Soluble | |
| 9 | toluene | 200 | Insoluble | Amorphous |
| 10 | dichloromethane | 5 | Soluble | Amorphous |
| 11 | chloroform | 5 | Soluble | Amorphous |
| 12 | TBME | 200 | Insoluble | Amorphous |
| 13 | isopropyl acetate | 200 | Insoluble | Amorphous |
| 14 | 4-methyl-2-pentanone | 200 | Insoluble | Amorphous |
| 15 | THF | 100 | Soluble | Amorphous |
| 16 | 10% EtOAc/ cyclohexane | 200 | Insoluble | Amorphous |

Figure 11:
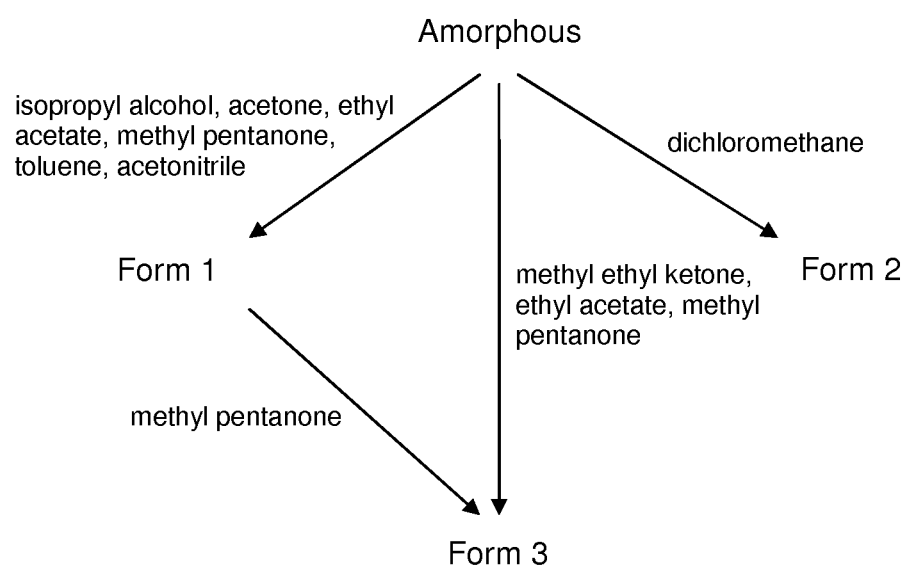
FIG. 11 provides a scheme for preparing polymorphs of a tosylate salt of Compound 1.

A summary of the polymorphism a tosylate salt of Compound 1 is presented in FIG. 11.

Figure 4:
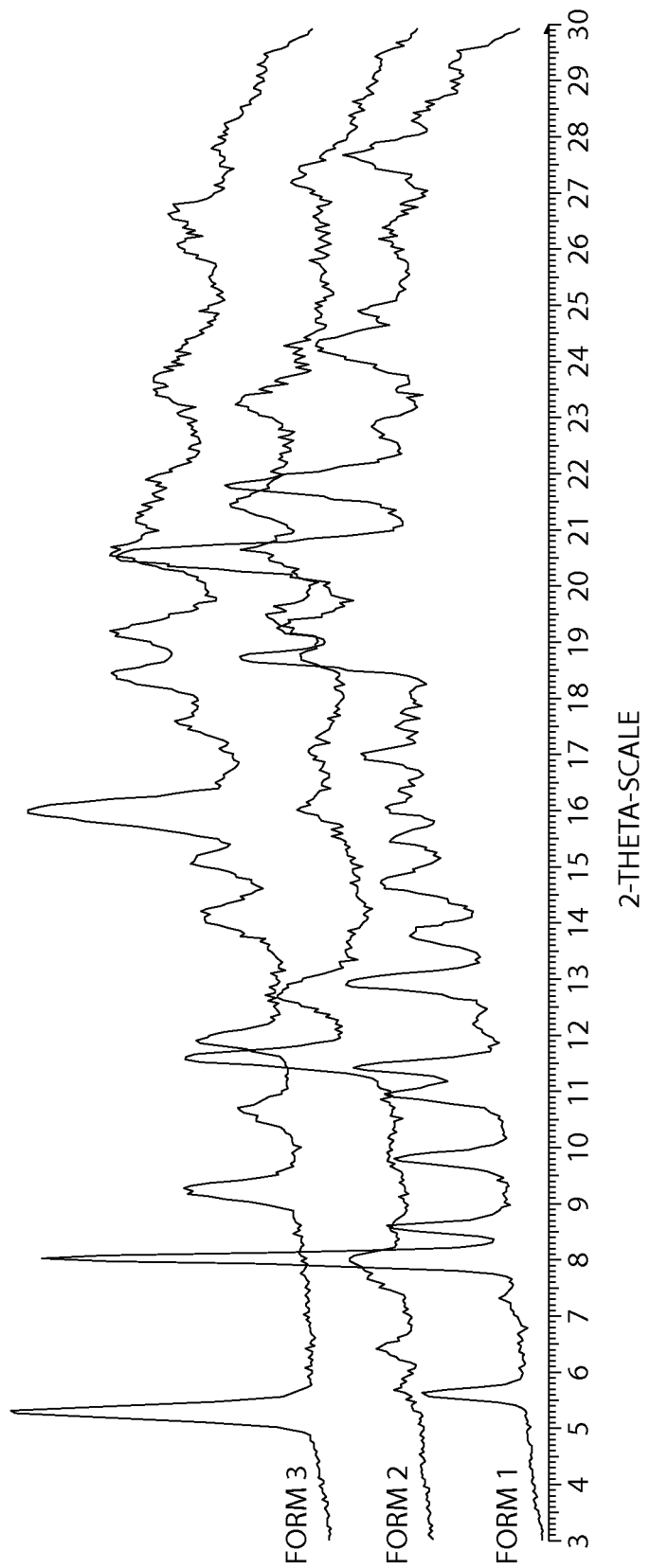
FIG. 4 provides a comparison of X-ray powder diffraction patterns at 25° C. for samples comprising form 1 tosylate salt, form 2 tosylate salt, and form 3 tosylate salt that were dried overnight in a vacuum.

After recrystallization, samples of form 1, form 2, and form 3 tosylate salt were dried overnight in a vacuum and analyzed by XRPD, as shown in FIG. 4. There was no change in form after drying.

Figure 5:
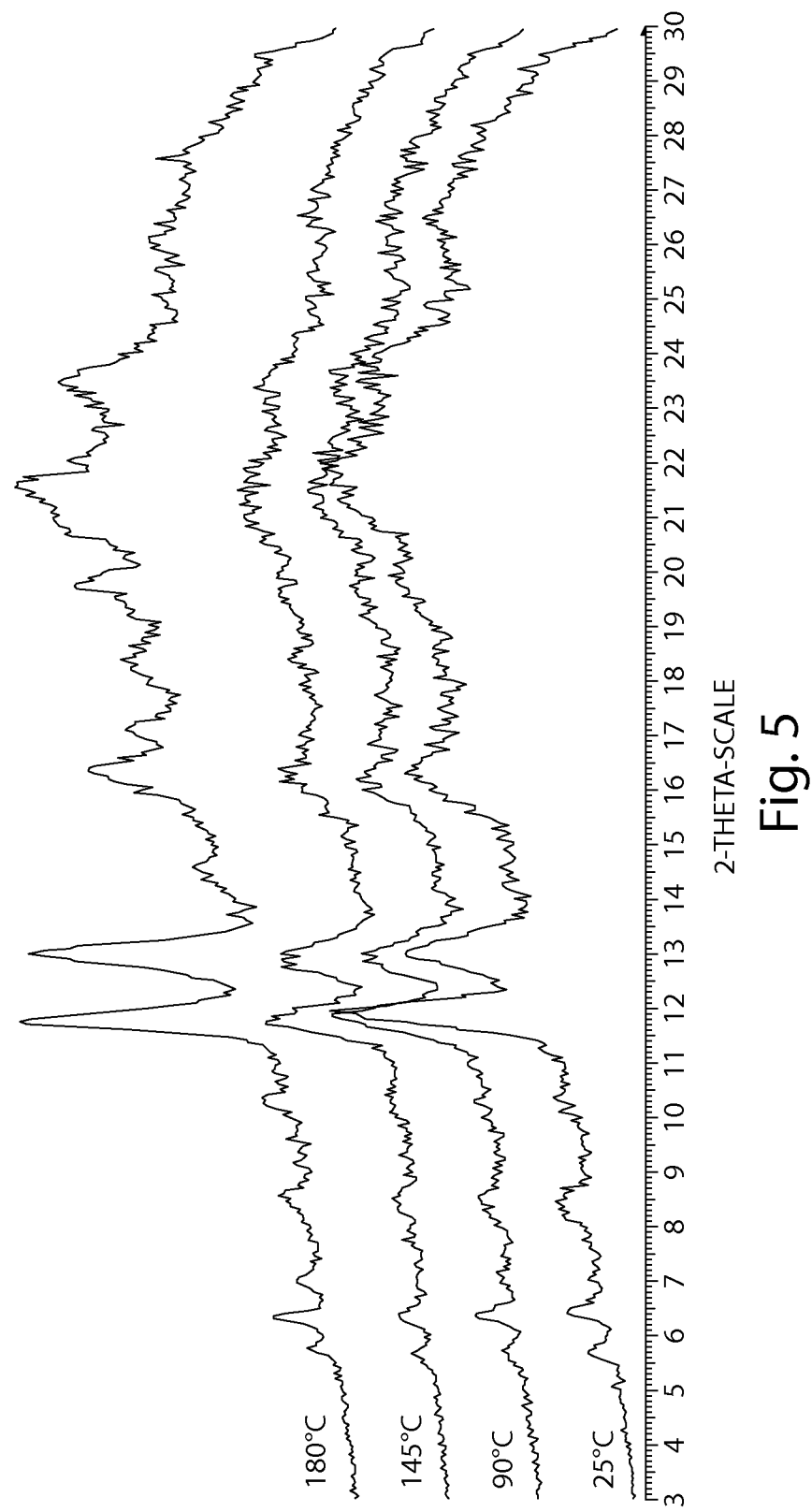
FIG. 5 provides a variable temperature X-ray powder diffraction analysis of samples comprising form 2 tosylate salt.
Figure 6:
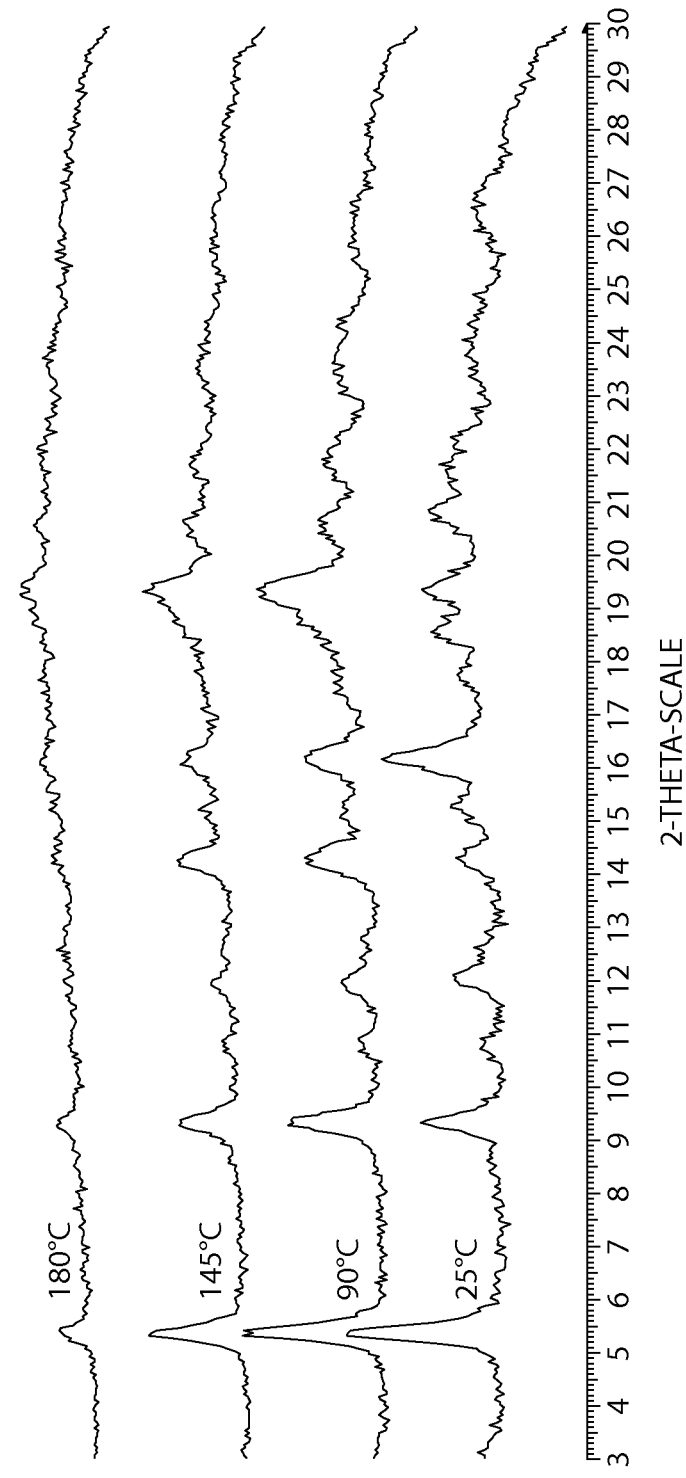
FIG. 6 provides a variable temperature X-ray powder diffraction analysis of samples comprising form 3 tosylate salt.

Variable temperature XRPD was performed on form 2 and form 3 tosylate salt of Compound 1. See FIG. 5 and FIG. 6, respectively.

Figure 7:
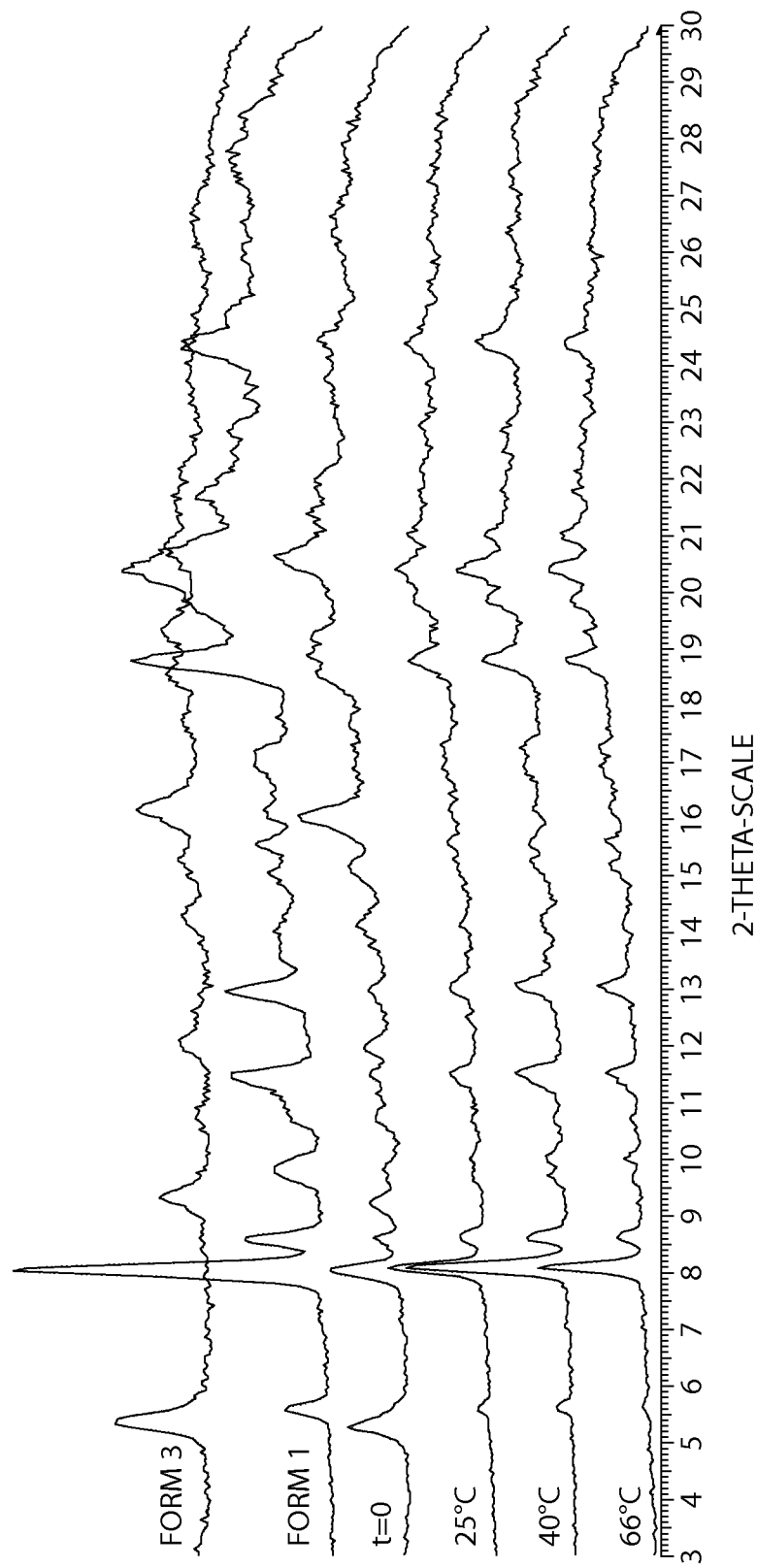
FIG. 7 provides a variable temperature X-ray powder diffraction analysis of samples comprising a slurry of a 50:50 mixture of form 1 tosylate salt and form 3 tosylate salt in IPA.

The relative stabilities of the polymorphic forms of Compound 1 were analyzed. For example, form 1 tosylate salt was subjected to a maturation experiment for 24 hours in either IPA or methyl pentanone, seeded with either form 2 or form 3 tosylate salt. During this experiment, there was no change of form 1 into form 2 or 3. A slurry of a 50:50 mixture of form 1 and form 3 were analyzed in IPA for 18 hours at 0° C., 25° C., 40° C., and 60° C., as shown in FIG. 7. There was no change of form 1 into form 3.

Recrystallization experiments indicated that form 1 tosylate salt can be obtained reproducibly from the amorphous tosylate salt by slurrying in IPA. Form 1 of Compound 1 can also be obtained reproducibly by the addition of tosic acid. A high resolution XRPD scan of form 1 is depicted in FIG. 8 and the characteristic of the diffraction pattern are shown Table 1.

4. Pharmaceutical Compositions Comprising Compounds, Salts, Crystalline Forms or Polymorphs Thereof of the Invention In a further embodiment, the invention pertains to pharmaceutical compositions comprising a tetracycline compound of the invention (e.g., synthesized, or purified by the methods of the invention) or a pharmaceutically acceptable salt, prodrug or ester thereof. The pharmaceutical compositions may comprise a pharmaceutically acceptable carrier.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant the diluent, excipient or carrier must be compatible with the other ingredients of the formulation and not deleterious to the recipient thereof.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" is recognized in the art and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts, and the like. (See, e.g., Berge et al. (1977) "Pharmaceutical Salts", *J. Farm. SCI.* 66:1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances includes relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine, and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters. (See, for example, Berge et al., supra.).

The invention also pertains to tetracycline compounds, which are synthesized and/or purified by the methods of the invention, and pharmaceutically acceptable salts thereof.

The phrase "pharmaceutically acceptable carrier" is recognized in the art and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, releasing agents, coating agents, sweetening agents, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate and/or any of the following: fillers or extenders, such as starches, lactose, sucrose, glucose, mannitol and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening agents, flavoring agents, coloring agents, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The preparations of the present invention may be given orally, parenterally, topically or rectally. They are given by forms suitable for each administration route. For example, they are administered in tablets or capsule form. For example, they are administered by injection, infusion, inhalation, lotion, ointment, suppository, etc. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration", "administered systemically", "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally (as by, for example, a spray), rectally, intravaginally, parenterally, intracisternally and topically (as by powders, ointments or drops, including buccally and sublingually).

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

The term "therapeutically effective amount" refers to the amount of the subject salt or polymorph that will elicit the biological or medical response of a tissue, system, animal or human that is being sought by the researcher, veterinarian, medical doctor or other clinician or that is sufficient to prevent development of or alleviate to some extent one or more of the symptoms of the disease being treated.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 10 mg per kg per day. For example, in some embodiments the doses are between 0.5 and 4.0 mg per kg day. If desired, the effective daily dose of the active compound may be administered as one, two, three, four, five, six or more sub-doses administered separately at appropriate intervals throughout the day or week or other suitable time period, optionally, in unit dosage forms.

While it is possible for a compound of the present invention to be administered alone, it is preferable to administer the compound as a pharmaceutical composition.

5. Methods of Using the Tetracycline Compounds of the Invention

The invention also pertains to a method for treating a tetracycline responsive state in a subject, by administering to the subject an effective amount of a composition comprising a Compound 1 according to the invention or a pharmaceutically acceptable salt thereof, such that the state is treated.

The terms "treat", "treating" or "treatment", as used herein, refer to a method of alleviating or abrogating a disease or disorder (e.g., the tetracycline compound responsive state) and/or its attendant symptoms. The terms "prevent", "preventing" or "prevention", as used herein, refer to a method of barring a subject from acquiring a disease or disorder. The "subject", as used herein, includes a mammal. The mammal can be e.g., any mammal, e.g., a human, primate, mouse, rat, dog, cat, cow, horse, goat, camel, sheep or a pig. Preferably, the mammal is a human.

The language "tetracycline compound responsive state" or "tetracycline responsive state" includes states which can be treated, prevented, or otherwise ameliorated by the administration of a tetracycline compound of the invention. Tetracycline compound responsive states include bacterial, viral, and fungal infections (including those which are resistant to other tetracycline compounds), cancers (e.g., prostate cancer, breast cancer, colon cancer, lung cancer, melanoma, lymph cancers and other disorders characterized by unwanted cellular proliferation, including, but not limited to, those described in U.S. Pat. No. 6,100,248), arthritis, osteoporosis, diabetes, and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 1998, 48:6686-6690). In one embodiment, the tetracycline responsive state is not a bacterial infection. In another embodiment, the tetracycline compounds of the invention are essentially non-antibacterial. For example, non-antibacterial tetracycline compounds of the invention may have MIC values greater than about 4 µg/ml as measured by assays known in the art.

Tetracycline compound responsive states also include inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or present in an area in aberrant amounts. The inflammatory process is the response of living tissue to damage. The cause of inflammation may be due to physical damage, chemical substances, micro-organisms, tissue necrosis, cancer or other agents. Acute inflammation is short-lasting for only a few days. If it is longer lasting, however, then it may be referred to as chronic inflammation.

IPAS's include inflammatory disorders. Inflammatory disorders are generally characterized by heat, redness, swelling, pain or loss of function. Examples of causes of inflammatory disorders include, but are not limited to, microbial infections (e.g., bacterial and fungal infections), physical agents (e.g., burns, radiation and trauma), chemical agents (e.g., toxins and caustic substances), tissue necrosis and various types of immunologic reactions. In a further embodiment, the IPAS includes disorders described in U.S. Pat. Nos. 5,929,055 and 5,532,227, incorporated herein by reference in their entirety.

Examples of inflammatory disorders include, but are not limited to, osteoarthritis, rheumatoid arthritis, acute and chronic infections (bacterial and fungal, including diphtheria and pertussis), acute and chronic bronchitis, sinusitis, upper respiratory infections (the common cold, etc.), acute and chronic gastroenteritis and colitis, acute and chronic cystitis and urethritis, acute and chronic dermatitis, acute and chronic conjunctivitis, acute and chronic serositis (pericarditis, peritonitis, synovitis, pleuritis and tendinitis), uremic pericarditis, acute and chronic cholecystis, acute and chronic vaginitis, acute and chronic uveitis, drug reactions, insect bites, burns (thermal, chemical and electrical) and sunburn.

The term "inflammatory process associated state" includes, in one embodiment, NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Other examples of NO associated states include, but are not limited to, malaria, senescence, diabetes, vascular stroke, neurodegenerative disorders (Alzheimer's disease, Huntington's disease and Parkinson's disease), cardiac disease (reperfusion-associated injury following infarction), juvenile diabetes, inflammatory disorders, osteoarthritis, rheumatoid arthritis, acute, recurrent and chronic infections (bacterial, viral and fungal), acute and chronic bronchitis, sinusitis, and respiratory infections (the common cold, etc.), acute and chronic gastroenteritis and colitis, acute and chronic cystitis and urethritis, acute and chronic dermatitis, acute and chronic conjunctivitis, acute and chronic serositis (pericarditis, peritonitis, synovitis, pleuritis and tendonitis), uremic pericarditis, acute and chronic cholecystis, cystic fibrosis, acute and chronic vaginitis, acute and chronic uveitis, drug reactions, insect bites, burns (thermal, chemical and electrical), and sunburn.

The term "inflammatory process associated state" also includes, in one embodiment, matrix metalloproteinase associated states (MMPAS). MMPAS include states characterized by aberrant amounts of MMPs or MMP activity. These are also included as tetracycline compound responsive states which may be treated using compounds of the invention.

Examples of matrix metalloproteinase associated states (MMPAS's) include, but are not limited to, arteriosclerosis, corneal ulceration, emphysema, osteoarthritis, multiple sclerosis (Liedtke et al., *Ann. Neurol.* 1998, 44:35-46; Chandler et al., *J. Neuroimmunol.* 1997, 72:155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., *Annu. Rev. Cell Biol.* 1993, 9:541-73; Tryggvason et al., *Biochim. Biophys. Acta* 1987, 907:191-217; Li et al., *Mol. Carcinog.* 1998, 22:84-89), metastasis, acute lung injury, stroke, ischemia, diabetes, aortic or vascular aneurysms, skin tissue wounds, dry eye, bone and cartilage degradation (Greenwald et al., *Bone* 1998, 22:33-38; Ryan et al., *Curr. Op. Rheumatol.* 1996, 8:238-247). Other MMPAS include those described in U.S. Pat. Nos. 5,459,135; 5,321,017; 5,308,839; 5,258,371; 4,935,412; 4,704,383; 4,666,897 and RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the compounds of the invention include, but are not limited to, carcinomas of the prostate, breast, ovary, testis, lung, colon and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes and colon.

In an embodiment, the invention pertains to a method for treating a subject suffering or at risk of suffering from cancer, by administering an effective amount of a substituted tetracycline compound such that inhibition of cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

Examples of tetracycline responsive states also include neurological disorders which include both neuropsychiatric and neurodegenerative disorders, but are not limited to, Alzheimer's disease, dementias related to Alzheimer's disease such as Pick's disease, Parkinson's diseases and other Lewy diffuse body diseases, senile dementia, Huntington's disease, Gilles de la Tourette's syndrome, multiple sclerosis, amylotrophic lateral sclerosis (ALS), progressive supranuclear palsy, epilepsy, and Creutzfeldt-Jakob disease, autonomic function disorders such as hypertension and sleep disorders, neuropsychiatric disorders (depression, schizophrenia, schizoaffective disorder, Korsakoff's psychosis, mania, anxiety disorders, phobic disorders, etc.), learning or memory disorders (amnesia or age-related memory loss, attention deficit disorder, etc.), dysthymic disorder, major depressive disorder, obsessive-compulsive disorder, psychoactive substance use disorders, anxiety, phobias, panic disorder, as well as bipolar affective disorder (severe bipolar affective (mood) disorder (BP-1), bipolar affective neurological disorders, e.g., migraine and obesity, etc.). Further neurological disorders include, for example, those listed in the American Psychiatric Association's Diagnostic and Statistical manual of Mental Disorders (DSM), the most current version of which is incorporated herein by reference in its entirety.

In another embodiment, the tetracycline compound responsive state is diabetes, e.g., juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy.

In another embodiment, the tetracycline compound responsive state is a bone mass disorder. Bone mass disorders include disorders where a subjects bones are disorders and/or states where the formation, repair or remodeling of bone is advantageous. For example, bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227 and 4,666,897, each of which is hereby incorporated herein by reference in its entirety.

In another embodiment, the tetracycline compound responsive state is acute lung injury. Acute lung injuries include adult respiratory distress syndrome (ARDS), post-pump syndrome (PPS) and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a substituted tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited to, asthma, cystic fibrosis and emphysema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke or ischemic stroke. The invention also pertains to a method for treating ischemia, stroke or ischemic stroke by administering an effective amount of a substituted tetracycline compound of the invention. In a further embodiment, the tetracycline compounds of the invention are used to treat such disorders as described in U.S. Pat. Nos. 6,231,894; 5,773,430; 5,919,775 and 5,789,395, incorporated herein by reference.

In another embodiment, the tetracycline compound responsive state is a skin wound. The invention also pertains, at least in part, to a method for improving the healing response of the epithelialized tissue (e.g., skin, mucusae, etc.) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gellatinolytic activity of MMPs. In a further embodiment, the tetracycline compound of the invention is administered to the surface of the skin (e.g., topically). In a further embodiment, the tetracycline compound of the invention used to treat a skin wound, and other such disorders as described in, for example, U.S. Pat. Nos. 5,827,840; 4,704,383; 4,935,412; 5,258,371; 5,308,8391 5,459,135; 5,532,227 and 6,015,804, each of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may be effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the in vitro standard broth dilution method described in Waitz, J. A., *National Commission for Clinical Laboratory Standards, Document M7-A2*, vol. 10, no. 8, pp. 13-20, $2^{nd}$ edition, Villanova, Pa. (1990).

The tetracycline compounds may also be used to treat infections traditionally treated with tetracycline compounds such as, for example, rickettsiae infection, a number of gram-positive and gram-negative bacterial infection, lymphogranuloma venereum, inclusion conjunctivitis and psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "in combination with" another therapeutic agent or treatment includes co-administration of the tetracycline compound, (e.g., inhibitor) and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent which is known in the art to treat, prevent, or reduce the symptoms of a disease or disorder, such as IPAS. Furthermore, the other therapeutic agent may be any agent of benefit to the patient when administered in combination with the administration of a tetracycline compound. In one embodiment, the diseases, such as cancer, treated by methods of the invention include those described in U.S. Pat. Nos. 6,100,248; 5,843,925; 5,837,696 and 5,668,122, incorporated herein by reference in their entirety.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

The invention is further illustrated by the following examples, which should not be construed as further limiting.

6. Exemplification of the Invention

Example 1

Synthesis of 9-Alkyl Aminomethyl Minocycline

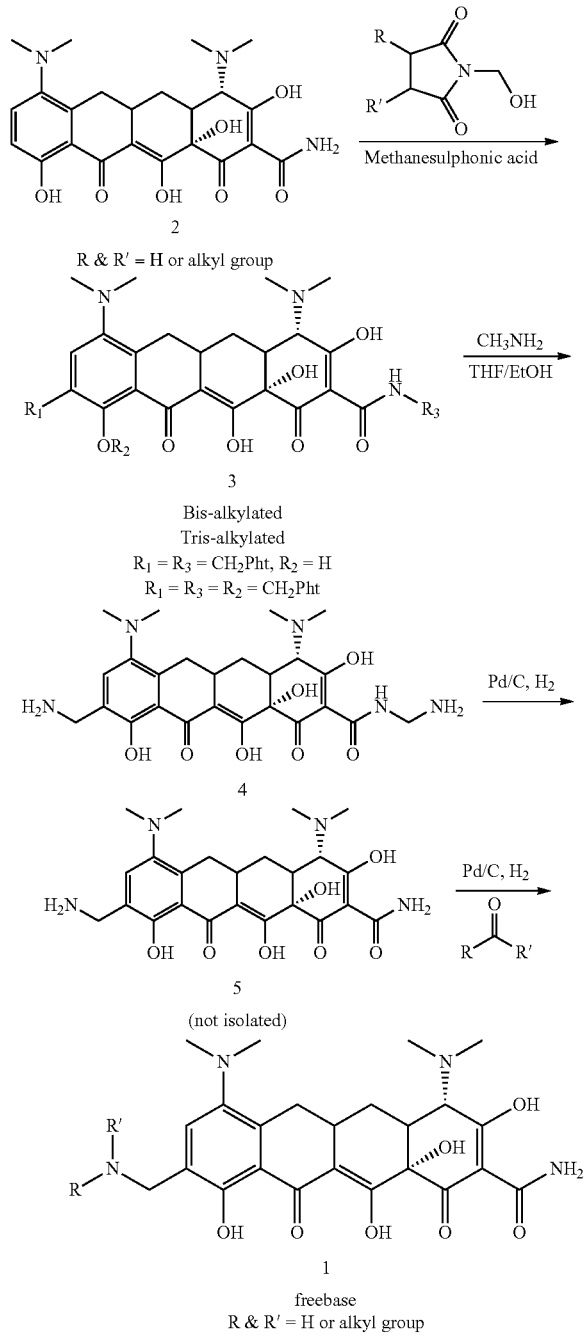

Minocycline hydrochloride (compound 2) was dissolved in methylsulfonic acid or hydrofluoric acid with methylsulfonic anhydride or similar water scavenger acid such as triflic acid. N-hydroxymethyl phthalimide was added to the reaction mixture. The mixture was stirred at 20-35° C. until the reaction was complete. The acid solution was added to an ice/water mixture, and triflic salt can be readily precipitated, filtered and collected. The solid was re-dissolved in acetone and brought to a neutral pH with base. The product was precipitated by the addition of water. If the triflic acid was present as scavenger the product can be precipitated without neutralization. The product was isolated as a mixture of the bis and tris alkylated product. The isolated material of this reaction was enriched in the desired bis ratio (90%).

The solid was suspended in the EtOH or MeOH. Aminolysis was carried out by using methylamine. A phthalamide by-product precipitated as the reaction progressed and was removed by filtration. The light yellow solid product was precipitated out by the addition of about 1.5 volumes of t-butylmethylether to the reaction mixture, and collected through a simple filtration that left many small impurities and methylamine reagent in the solution. Further purification of the compound was performed through re-slurrying with a lower aliphatic alcohol such as methanol.

Compound 4 as freebase was transferred to a hydrogenation vessel which was charged with methanol and aldehyde. An inactivated Pd/C catalyst was charged and the vessel was pressurized with hydrogen gas. The reaction mixture was hydrogenated under hydrogen pressure around 30 Psi for about 24 hours. When conversion of compound 4 to 1 was complete, the solution was filtered and washed through a Celite pad. At this point the reaction mixture contained very low β C-4 epimer, around 3-7%.

The product (1) was worked up as follows to isolate the product selectively from its impurities. The pH of the solution was adjusted to about 4.5 with concentrated HCl and the solution was extracted with dichloromethane. The aqueous layer was extracted with dichloromethane to selectively recover the preferred epimer product (e.g., α). The dichloromethane layers were combined and concentrated, and 2 L of n-heptane was added to precipitate the product. Further purification was obtained by repeating the work-up procedure with or without t-butylmethylether to dissolve the crude product.

Example 2

Purification of Compound 1

Crude 9-(2',2'-dimethylpropyl aminomethyl) minocycline freebase (40 g) was dissolved in 150 mL of buffer A (0.1% aqueous solution of methanesulfonic acid—MSA) and the pH was adjusted to 2-3 with MSA.

The solution was filtered and injected into an HPLC and the product was eluted with an isocratic gradient of 94% buffer A and 6% acetonitrile. The product fraction collection was initiated when the product peak was detected. Each fraction was analyzed and an acceptance criterion of greater than 80% AUC of the main peak was used for the early product fractions. When combining fractions, the level of impurities and relative concentration of the pooled fractions was factored into the selection criteria that meet the final product specifications. To the product fractions was added a 10% aqueous solution of sodium sulfite equal to 10% of the original volume of the collected fractions.

The following example represents the output of a single injection. The output from multiple injections may also be combined and worked up. A product fraction volume of 3.5 L (including sodium sulfite) was collected and the pH was adjusted to 4.0-4.5 using a solution of sodium hydroxide. The aqueous solution was washed with 2 L of dichloromethane and the organic layer was separated and discarded.

The pH of the aqueous layer is adjusted to 7.5-8.5 using sodium hydroxide and the product was extracted four times with 2.4 L of dichloromethane. The pH was readjusted to 7.5-8.5 with sodium hydroxide or MSA, prior to each extraction.

The four dichloromethane layers were combined and concentrated to about 200 mL, which was then added slowly (over a period of about 10 minutes) to a vigorously stirred n-heptane (2.5 L). The suspension was stirred for about 10 minutes at room temperature and diluted slowly (over a period of 5 minutes) with n-heptane 1.5 L. The slurry is cooled to 0-5° C. and stirred for 1-2 hours. The suspended solid was filtered and washed with 3×150 mL portions of n-heptane. The product was dried under vacuum at 40° C. for at least 24 hours until a constant weight was achieved and the levels of all residual solvents were within specification. Approximately 13.6 g of 9-(2',2'-dimethylpropyl aminomethyl) minocycline freebase was isolated as a yellow solid.

Example 3

Preparation of Crystalline HCl Salt of Compound 1

Compound 1 (13 g) was dissolved in acetone (300 mL), filtered and the filter was additionally washed with acetone. The combined filtrate and washes was cooled to 5° C. To the combined filtrate and washes, a solution of concentrated HCl (3.9 mL) in acetone (79 mL) was slowly added with vigorous stirring. The resultant slurry was stirred in an ice bath for 15 minutes and filtered off.

The first crop of solid was washed with cold acetone and pentane and dried in vacuo for 48 hours, yielding 13.7 g of yellow amorphous solid. The flask with saturated filtrate was covered with aluminum foil and left for 2 weeks during which the growth of single crystals was observed. Crystals were collected by filtration and washed with hexane.

Example 4

Preparation of Crystalline Methanesulfonic Acid Salt of Compound 1

To a 25-mL 3-neck flask under an inert nitrogen atmosphere, 3 mL of isopropanol (IPA) was charged. A slurry was prepared by adding 225 mg amorphous free base of Compound 1 to the flask. The slurry was warmed to a temperature of 45° C. Methanesulfonic acid hydrate (98.0 mg) was then added to the slurry. The slurry was stirred at 45° C. for one hour, then cooled to 22° C. to produce a thick crystalline slurry. The slurry was filtered and washed with IPA (2×1 mL). Excess IPA was removed from the crystalline cake by drying at 55° C. for more than two hours to achieve a constant weight. Crystalline mesylate (methanesulfonic acid) salt of Compound 1 (180 mg) was isolated. It was determined that the crystalline mesylate salt was unstable at 5° C.

Example 5

Preparation of Crystalline Tosylate Salt of Compound 1 (Using a Slurry Method)

To a 5-L 3-neck flask under an inert nitrogen atmosphere, 2.0 L of isopropanol (IPA) was charged. A slurry was prepared by adding 289 g of the amorphous free base of Compound 1 to the flask. A solution of p-toluenesulfonic acid hydrate (97.0 g) in IPA (400 mL) was then added to the slurry. The water content of the slurry supernatant was adjusted to 0.6 g/L with the addition of water (9 mL), and the slurry was stirred at 20-25° C. for 18 hours to produce a thick crystalline slurry. The slurry was filtered and washed with IPA (2×500 mL). Excess IPA was removed from the crystalline cake by blowing dry nitrogen through the cake for 24 hours. With the solids containing 3 weight-percent (wt %) of IPA, the cake was further dried by blowing humidified nitrogen through the cake at a relative humidity of 70-75% for 24 hours. The cake retained 0.9 wt % of IPA that was not further reduced by this method. Excess water was then removed from the cake by blowing dry nitrogen through the cake for 24 hours. The tosylate salt of Compound 1 was isolated as an orange powder (337 g). The isolated tosylate salt of Compound 1 was crystalline with only one observed form: a non-stoichiometric hemihydrate, as determined by x-ray powder diffraction (XPRD) and thermogravimetric (TG) analysis.

Example 6

Preparation of Crystalline Tosylate Salt of Compound 1 (Using a Solution Method)

To a 5-L 3-neck flask under an inert nitrogen atmosphere, 1.7 L of methanol and 1.7 L of methyl-t-butyl ether were charged. P-toluene sulfonic acid monohydrate (209 g) and the amorphous free base of Compound 1 (556 g) were added with stirring to the flask to obtain a clear solution. A seed quantity (3 g) of the monotosylate salt of compound 1 was added to initiate crystallization and a further quantity of methanol (0.1 L) and methyl-t-butyl ether (0.5 L) was added. The resulting slurry was stirred at about 20° C. for 22 hours to produce a thick crystalline slurry. The slurry was filtered and washed with a mixture of 1.1 L of methanol and 1.3 L of methyl-t-butyl ether followed by methyl-t-butyl ether (2×2.4 L). The tosylate salt of Compound 1 was isolated as an orange powder. Excess solvent was removed from the crystalline cake by blowing dry nitrogen through the cake for 24 hours. The cake was then dried under vacuum at about 30° C. until the solids contained about 6 weight-percent (wt %) of solvent. The cake was further dried under vacuum at about 45° C. until the solids contained less than 3 weight-percent (wt %) of solvent. The isolated tosylate salt of Compound 1 was crystalline with the observed form 1 as determined by x-ray powder diffraction (XPRD).

Example 7

Characterization of Tosylate Salt of Compound 1

The XRPD pattern of the isolated tosylate salt of Compound 1 comprised 2θ values in degrees of 5.6, 8.0, 8.6, 11.4, 13.0, 15.5, 18.8, 20.4 and 24.5.

The crystalline tosylate salt was subjected to thermogravimetric (TG) analysis under nitrogen flow at a heating rate of 10° C./minute. A weight loss of 3.9% was observed up to 81.3° C., which was due to water loss.

Upon drying, water content in the crystalline tosylate salt of Compound 1 was calculated to be 0.5%. After standing at room temperature for 24 hours, this value increased to 5%. In contrast to the amorphous Compound 1, the crystalline tosylate salt of Compound 1 was stable for weeks and months at room temperature, maintaining a water content of approximately 5%.

The hygroscopicity of the subject crystalline tosylate salt was determined using a symmetric vapor sorption analyzer, and reported as wt % gained as a function of percent relative humidity (% RH) from 5% to 95% to 1%, at 5% intervals at 25.0° C. A maximum weight gain of 12 wt % at 95% RH, with slight hysteresis upon desorption, was observed, and a 2 wt % loss due to IPA was observed.

The crystalline tosylate salt was determined to have the solubilities summarized in Table 6 below. The solubilities were determined by mixing excess solids with solvent, at ambient temperature for two hours, followed by filtration of the supernatant. The supernatant concentration was determined by high-performance liquid chromatography (HPLC). Equilibration of 56.8 mg of the subject crystalline tosylate salt in 0.5 mL water and 122.1 mg of the subject crystalline tosylate salt in 1.0 mL water resulted in clear solutions. The pH of 122.1 mg of the subject crystalline tosylate salt in 1.0 mL of water was determined to be 5.70.

TABLE 6

| Solvent | Solubility (mg/mL) |
|---|---|
| Water | >100 |
| Acetonitrile | 5.9 |
| Methanol | 86.1 |
| IPA | 5.8 |

Example 8

XRPD of Compound 1

X-Ray Powder Diffraction patterns were collected on a Siemens D5000 diffractometer using Cu Kα radiation (40 kV, 40 mA), θ-θ goniometer, divergence of V20 and receiving slits, a graphite secondary monochromator and a scintillation counter. The instrument is performance checked using a certified Corundum standard (NIST 1976). The software used for data collection was Diffrac Plus XRD Commander v2.3.1 and the data were analyzed and presented using Diffrac Plus EVA v 11.0.0.2 or v 13.0.0.2.

Powder samples were prepared as flat plate specimens using. Approximately 35 mg of the sample was gently packed into a cavity cut into polished, zero-background (510) silicon wafer. The sample was rotated in its own plane during analysis. The details of the data collection are:
 Angular range: 2 to 42°2θ
 Step size: 0.05°2θ
 Collection time: 4 s/step.
High resolution X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm.

The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically, the sample would be exposed to the X-ray beam for 120 seconds. The software used for data collection was GADDS for WNT 4.1.16 and the data were analyzed and presented using Diffrac Plus EVA v 9.0.0.2 or v 13.0.0.2.

Example 9

Temperature and Moisture Stability Study

A stability study was conducted on tosylate salt and mesylate salt of Compound 1, by monitoring changes in the high performance liquid chromatography (HPLC) impurity profiles for each salt when exposed to various temperatures and/or humidity conditions. Each sample was placed in a closed container and exposed to three controlled environments: refrigerated (5° C.), 20° C. and 60% relative humidity, and 40° C. and 75% relative humidity. After two weeks, the crystalline tosylate salt was determined to be the most stable crystalline form of Compound 1. The stability study of the crystalline tosylate salt was continued.

Samples were analyzed by the following reversed-phase HPLC impurity profile method at time points 0, 1, 2, 4 weeks (Table 7) and 3 months (Table 8) for the tosylate salt; and 0, 1 and 2 weeks for the mesylate salt (Table 9).

Reversed-phase HPLC analysis was conducted using a SYMMETRY SHIELD RP18 column (4.6×250 mm, 5 pm particle size), although analysis using a similar or equivalent column would be expected to yield similar results. The mobile phase components were 0.01 M ammonium acetate in water at pH 3.3 (A) and acetonitrile (B). The mobile phase composition was a gradient that increased from 6% to 15% B in five minutes, held at 15% B for 15 minutes, increased from 15% to 60% B in ten minutes, then from 60% to 90% B in two minutes, and then the system was re-equilibrated at 6% B for four minutes. The flow rate was 1.0 mL/minute, and the injection volume was 10.0 μL. The column temperature was maintained at 30° C. Detection was by ultraviolet light (UV) at 280 nm. The retention time for Compound 1 was approximately 15.7 minutes. The sample solution was prepared in mobile phase A to a final concentration of 2.0 mg/mL.

TABLE 7

| Time Point | Total Impurities** | RRT 0.52 (%) | RRT 0.77 (%) | RRT 0.93 (%) | RRT 1.19 (%) | RRT*** 1.26 (%) | RRT 1.77 (%) | Compound 1 (%) |
|---|---|---|---|---|---|---|---|---|
| Initial | 1.60 | 0.06 | ND | ND | 0.24 | 1.2 | 0.10 | 98.4 |
| 1 week | | | | | | | | |
| 5° C. | 1.51 | 0.09 | ND | ND | 0.21 | 1.1 | 0.11 | 98.5 |
| 20° C. & 60% RH* | 1.63 | 0.09 | ND | ND | 0.21 | 1.2 | 0.12 | 98.3 |
| 40° C. & 75% RH | 1.80 | 0.09 | 0.05 | ND | 0.21 | 1.3 | 0.14 | 98.2 |
| 2 weeks | | | | | | | | |
| 5° C. | 1.62 | 0.08 | ND | 0.08 | 0.24 | 1.1 | 0.12 | 98.4 |
| 20° C. & 60% RH | 1.66 | 0.08 | ND | 0.08 | 0.25 | 1.1 | 0.15 | 98.4 |
| 40° C. & 75% RH | 1.68 | 0.08 | ND | 0.09 | 0.25 | 1.1 | 0.16 | 98.3 |
| 4 weeks | | | | | | | | |
| 5° C. | 1.61 | 0.09 | 0.08 | 0.07 | 0.23 | 1.0 | 0.14 | 98.3 |
| 20° C. & 60% RH | 1.84 | 0.10 | 0.10 | 0.12 | 0.24 | 1.1 | 0.18 | 98.2 |
| 40° C. & 75% RH | 1.96 | 0.10 | 0.17 | 0.13 | 0.26 | 1.1 | 0.20 | 98.1 |

*RH denotes relative humidity
**Total impurities included all impurities in a specific batch
***RRT 1.26 denotes beta-epimer.

TABLE 8

| | 20° C. & 60% RH* | | | | 40° C. & 75% RH | | | |
|---|---|---|---|---|---|---|---|---|
| Time Point | Beta-epimer RRT = 1.26 | 4-keto compound RRT = 1.57 | M-2 impurity RRT = 0.84 | Total impurity** | Beta-epimer RRT = 1.26 | 4-keto compound RRT = 1.57 | M-2 impurity RRT = 0.84 | Total impurity |
| 0 month | 1.76% | 0.05% | — | 2.12% | 1.76% | 0.05% | — | 2.12% |
| 3 month | 1.74% | 0.10% | 0.18% | 2.86% | 1.66% | 0.14% | 0.31% | 3.12% |

*RH denotes relative humidity
**Total impurities included all impurities in a specific batch

TABLE 9

| Time Point | Total Impurities (%) | RRT 0.52 (%) | RRT 0.77 (%) | RRT 0.93 (%) | RRT 1.19 (%) | RRT 1.26 (%) | RRT 1.77 (%) | Compound 1 (%) |
|---|---|---|---|---|---|---|---|---|
| Initial | 1.70 | ND | ND | ND | 0.20 | 1.5 | ND | 98.3 |
| 1 week | | | | | | | | |
| 5° C. | 1.85 | ND | ND | ND | 0.17 | 1.6 | 0.08 | 98.2 |
| 20° C. & 60% RH* | 2.06 | ND | ND | ND | 0.17 | 1.8 | 0.09 | 98.0 |
| 40° C. & 75% RH | 2.97 | 0.07 | 0.05 | ND | 0.16 | 2.6 | 0.09 | 97.1 |
| 2 weeks | | | | | | | | |
| 5° C. | 1.65 | ND | ND | 0.06 | 0.20 | 1.3 | 0.09 | 98.3 |
| 20° C. & 60% RH | 1.87 | ND | ND | 0.06 | 0.20 | 0.11 | 0.11 | 98.1 |
| 40° C. & 75% RH | 3.38 | 0.05 | 0.07 | 0.06 | 0.19 | 0.11 | 0.11 | 96.6 |

The above data demonstrates that the tosylate salt of Compound 1 is stable when stored refrigerated and/or 20° C. & 60% RH conditions for at least four weeks. The tosylate salt of Compound 1 is stable at temperature in a range from 0° C.-70° C., or in a range from 5° C.-50° C., or in a range from 20° C.-30° C.

Example 10

Photostability Study

A photostability study was conducted on the tosylate salt of Compound 1. Two samples were prepared in clear glass Petri dishes. One sample was wrapped in aluminum foil to serve as a control sample. Both samples were placed in the ES 2000 Environmental Light 10 Chamber and exposed to 12 kilolux of cool white fluorescent light for a total of 47 hours. Samples were then analyzed by HPLC impurity profile method, and the results are summarized in Table 10.

TABLE 10

| Sample | RRT 0.52 (%) | RRT 0.0.64 (%) | RRT 0.77 (%) | RRT 0.83 (%) | RRT 0.93 (%) | RRT 1.19 (%) | RRT 1.26 (%) | RRT 1.77 (%) | Compound 1 (%) |
|---|---|---|---|---|---|---|---|---|---|
| Control | 0.06 | ND | 0.08 | ND | 0.12 | 0.26 | 1.2 | 0.16 | 98.2 |
| Exposed | 0.06 | ND | 0.09 | ND | 0.13 | 0.26 | 1.1 | 0.16 | 98.2 |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

All patents, patent applications, and literature references cited herein are hereby expressly incorporated by reference.

The invention claimed is:

1. A method of preparing a stable crystalline tosylate salt of Compound 1:

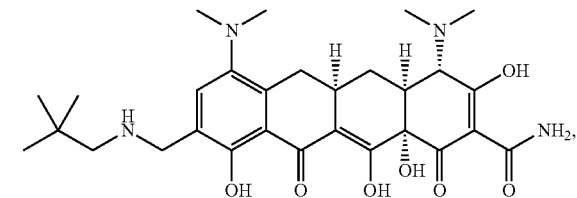

(1)

wherein the method comprises:
dissolving a freebase of Compound 1 in a first solvent or combination of solvents to form a first solution;
dissolving p-toluenesulfonic acid in a second solvent or combination of solvents to form a second solution;
combining the first and second solution to form a third solution;
adding a polymorph of a tosylate salt of Compound 1 to the third solution to form a fourth solution; and
crystallizing from the fourth solution a stable crystalline tosylate salt of Compound 1.

2. The method of claim 1, wherein the first solvent or combination of solvents and the second solvent or combination of solvents are the same.

3. The method of claim 1, wherein the first solvent or combination of solvents and the second solvent or combination of solvents are different.

4. The method of claim 1, wherein the first combination of solvents and the second combination of solvents are each independently a combination of alcoholic solvents.

5. The method of claim 4, wherein the first combination of solvents and the second combination of solvents are each independently a combination of two alcoholic solvents.

6. The method of claim 5, wherein the two alcoholic solvents are ethanol and isopropanol.

7. The method of claim 6, wherein the ethanol and isopropanol are at a volume-to volume ratio of 2 to 1.

8. The method of claim 1, wherein the first combination of solvents and the second combination of solvents each comprises an alcoholic solvent and an anti-solvent.

9. The method of claim 8, wherein the alcoholic solvent is methanol.

10. The method of claim 8, wherein the anti-solvent is selected from a ketone, an ester and an ether.

11. The method of claim 10, wherein the ether is methyl-t-butyl ether.

12. The method of claim 1, wherein the first combination of solvents and the second combination of solvents each consists of methanol and methyl-t-butyl ether.

13. The method of claim 12, wherein the methanol and methyl-t-butyl ether are at a volume-to-volume ratio of 1 to 1.2.

14. The method of claim 1, wherein the p-toluenesulfonic acid is provided in an amount of from 25 to 75 wt % relative to the amount of Compound 1.

15. The method of claim 1, wherein the p-toluenesulfonic acid is provided in a form of a p-toluenesulfonic acid monohydrate.

16. The method of claim 1, wherein the fourth solution forms a slurry upon stirring.

17. The method of claim 16, wherein the method further comprises drying the slurry.

18. The method of claim 1, wherein the polymorph is characterized by an X-ray powder diffraction pattern including peaks at approximately 8.06, 13.02, and 18.83 °2θ using Cu Kα radiation.

19. The method of claim 1, wherein the polymorph is characterized by an X-ray powder diffraction pattern including peaks at approximately 5.11 and 15.60 °2θ using Cu Kα radiation.

20. The method of claim 1, wherein the polymorph is characterized by an X-ray powder diffraction pattern including peaks at approximately 11.88 and 16.12 °2θ using Cu Kα radiation.

* * * * *